United States Patent
Begue et al.

(10) Patent No.: US 8,614,339 B2
(45) Date of Patent: Dec. 24, 2013

(54) DIMERIC DERIVATIVES OF ARTEMISININ AND APPLICATION IN ANTI-CANCER THERAPY

(75) Inventors: Jean-Pierre Begue, Paris (FR); Danièle Bonnet-Delpon, Paris (FR); Benoît Crousse, Igny (FR); Anaïs Fournial, Renaze (FR); Céline Mordant, Saint Julien en Genevois (FR); Jacques Fahy, Labruguiere (FR)

(73) Assignees: Pierre Fabre Medicament, Boulogne-Billancourt (FR); Centre National de la Recherche Scientifique (CNRS), Paris (FR); Universite Paris-Sud 11, Orsay (FR)

( * ) Notice: Subject to any disclaimer, the term of this patent is extended or adjusted under 35 U.S.C. 154(b) by 59 days.

(21) Appl. No.: 13/054,321

(22) PCT Filed: Jul. 29, 2009

(86) PCT No.: PCT/EP2009/059792
§ 371 (c)(1),
(2), (4) Date: Jan. 14, 2011

(87) PCT Pub. No.: WO2010/012761
PCT Pub. Date: Feb. 4, 2010

(65) Prior Publication Data
US 2011/0152289 A1  Jun. 23, 2011

(30) Foreign Application Priority Data
Jul. 29, 2008 (FR) ...................... 08 55201

(51) Int. Cl.
C07D 321/00 (2006.01)
(52) U.S. Cl.
USPC ........................................ 549/348
(58) Field of Classification Search
USPC ........................................ 549/348
See application file for complete search history.

(56) References Cited

FOREIGN PATENT DOCUMENTS

| FR | 760 266 A | 2/1934 | |
|---|---|---|---|
| WO | WO 03/035651 A2 | 5/2003 | |
| WO | WO 2007/116135 | * 10/2007 | ............ C07D 493/22 |
| WO | WO 2007/116135 A1 | 10/2007 | |

OTHER PUBLICATIONS

Fabienne et al. Organic Letters, vol. 7, No. 23, Jan. 1, 2005, pp. 5219-5222.*
Bonnet-Delpon et al. ACS symposium series, 2007, 949, 337-351.*
Chow et al. Current Pharmaceutical Design, 2009, vol. 15, No. 6, 659-674.*
Beekman et al., "Stereochemistry-Dependent Cytotoxicity of Some Artemisinin Derivatives," Journal of Natural Products, Apr. 1997, vol. 60, No. 4, pp. 325-330.
Begue et al., "Artemisia annua, Malaria in the world," Chem. Med. Chem., 2007, vol. 2, pp. 608-624.
Chorki et al., "First Synthesis of 10 alpha-(Trifluoromethyl)deoxoartemisinin," Organic Letters, 2002, vol. 4, No. 5, pp. 757-759.
Cree et al., Measurement of Cytotoxicity by ATP-based Luminescence Assay in Primary Cell Cultures and Cell Lines, Toxicology in Vitro, 1997, vol. 11, pp. 553-556.
Ekthawatchai et al., "C-16 Artemisinin Derivatives and Their Antimalarial and Cytotoxic Activities: Syntheses of Artemisinin Monomers, Dimers, Trimers, and Tetramers by Nucleophilic Additions to Artemisitene," J. Med. Chem., 2001, vol. 44, pp. 4688-4695.
Grellepois et al., "Orally Active Antimalarials: Hydrolytically Stable Derivatives of 10-Trifluoromethyl Anhydrodihydroartemisinin," J. Med. Chem., 2004, vol. 47, pp. 1423-1433.
Grellepois et al., "Synthesis of New Artemisinin-Derived Dimers by Self-Cross-Metathesis Reaction," Organic Letters, 2005, vol. 7, No. 23, pp. 5219-5222.
International Search Report in International Application No. PCT/EP2009/059792 mailed Sep. 8, 2009.
O'Neill et al., "A Medicinal Chemistry Perspective on Artemisinin and Related Endoperoxides," Journal of Medicinal Chemistry, 2004, vol. 47, No. 12.
Posner et al., "Antimalarial, Antiproliferative, and Antitumor Activities of Artemisinin-Derived, Chemically Robust, Trioxane Dimers," 1999, vol. 42, No. 21, pp. 4275-4280.
Posner et al., "Trioxane Dimers Have Potent Antimalarial, Antiproliferative and Antitumor Activities in Vitro," Bioorganic & Medicinal Chemistry, 1997, vol. 5, No. 7, pp. 1257-1265.
Sun et al., "Antitumor Activities of 4 Derivatives of Artemisic Acid and Artemisinin B in Vitro," Acta Pharmacol. Sin., 1992, vol. 13, No. 6, pp. 541-543, including an English abstract.
Woerdenbag et al., "Cytotoxicity of Artemisinin-related Endoperoxides to Ehrlich Ascites Tumor Cells," Journal of Natural Products, 1993, vol. 56, No. 6, pp. 849-856.

* cited by examiner

*Primary Examiner* — Nizal Chandrakumar
(74) *Attorney, Agent, or Firm* — Birch, Stewart, Kolasch & Birch, LLP.

(57) ABSTRACT

The present invention relates to dimeric derivatives of 10-trifluoromethylated artemisinin of formula (I) below: Formula (I) and the pharmaceutically acceptable salts thereof, and also to the preparation method thereof and to the uses thereof, especially in the treatment of cancer.

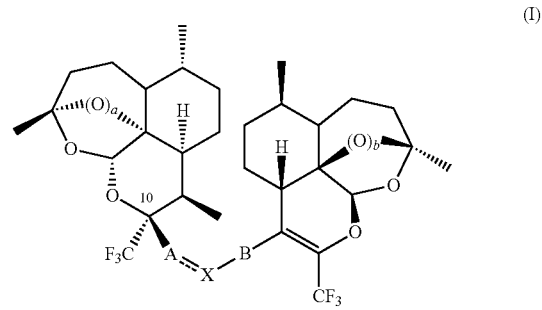

(I)

10 Claims, No Drawings

DIMERIC DERIVATIVES OF ARTEMISININ AND APPLICATION IN ANTI-CANCER THERAPY

The present invention relates to dimeric derivatives of 10-trifluoromethylartemisinin linked on the one hand by a carbon in position 10 and on the other hand by a carbon in position 16, and also to the use of same for treating cancer.

The cytotoxic properties of artemisinin derivatives were shown in 1992 [*Acta Pharmacol. Sin.*, 13, 541-3, (1992)], thus conferring to these compounds a potential use as an anticancer drug. It then turned out that dimeric derivatives of artemisinin had cytotoxic activities that were sometimes higher than those of the corresponding monomers [*J. Nat. Prod.*, 56, 849-56, (1993), *J. Nat. Prod.*, 60, 325-30, (1997)].

Consequently, much work aimed at preparing new artemisinin dimers was undertaken by several research teams across the globe. The majority of these dimers are dimmers in C-10, i.e. linked by their carbon in position 10, of dihydroartemisinin ether derivatives [*Bioorg. Med. Chem.*, 5, 1257-65, (1997)] or of more metabolically stable non-ketal analogs, in which the exocyclic oxygen atom of the ketal function was replaced by a $CH_2$ group (group X in the diagram below) [*J. Med. Chem.*, 42, 4275-80, (1999)]. Dimers in C-16 also have been described [*J. Med. Chem.*, 44, 4688-95, (2001)].

These various families are diagrammed below:

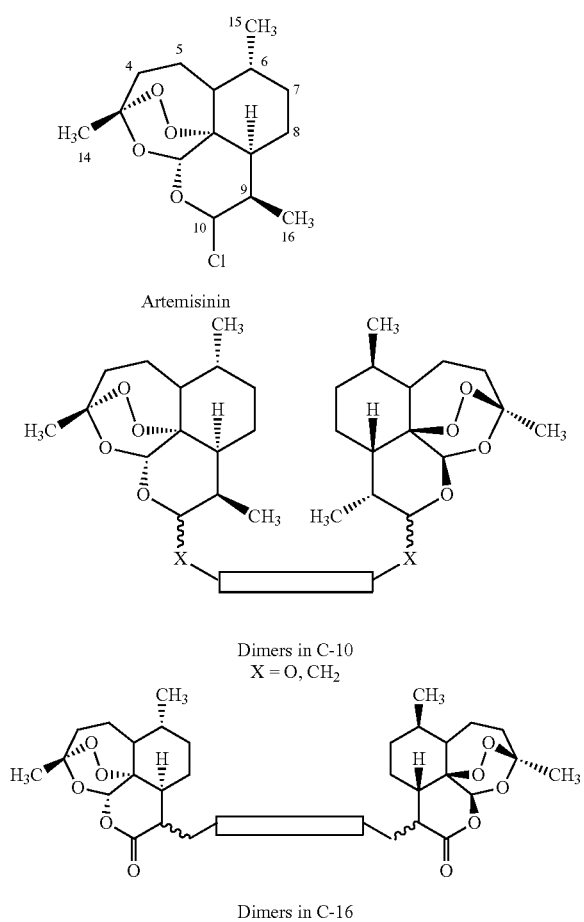

Artemisinin and its derrivatives such as artemether and sodium artesunate, the most well known, are widely used for treating malaria. However, the principal limitation of these derivatives rests in the low bioavailability of the artemisinin nucleus, whose ketal function is rapidly hydrolyzed in the body, thus leading to inactive metabolites [*J. Med. Chem.*, 47, 2945-64, (2994)].

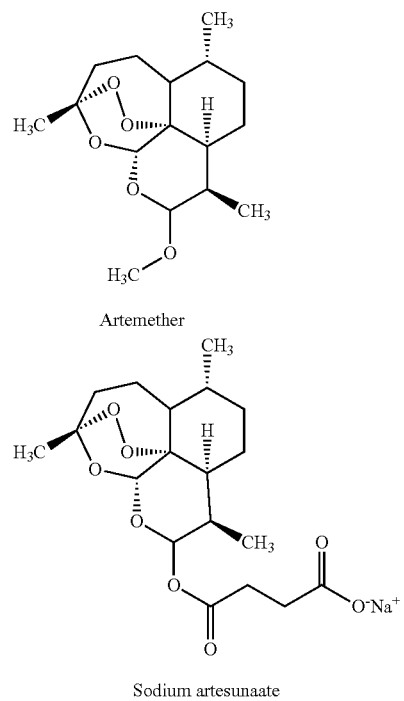

In the context of the search for new stable artemisinin derivatives for treating malaria, studies undertaken at the BioCIS Laboratory of the Chatenay-Malabry Faculty of Pharmacy (France) led to the synthesis of 10-trifluoromethylated artemisinin derivatives (WO 03/035 651). The introduction of a trifluoromethyl group stabilizes the ketal function, the consequence of which is to very significantly increase the stability of these compounds and to extend their duration of action, notably during administration of the compounds by oral route.

A recent review details with precision the chemical and pharmacological advantages of trifluoromethylated artemisinin derivatives [J.-P. Bégué, D. Bonnet-Delpon, *ChemMedChem*, 2, 608-24, (2007)].

A first series of 10-trifluoromethylartemisinin dimers linked by their carbon atoms in position C16 was developed with satisfactory anti-proliferative activity profiles (application FR 07/60 266).

The present invention more specifically relates to 10-trifluoromethylartemisinin dimers linked in position C10 on one nucleus and C16 on the other nucleus, compounds which exhibit better cytotoxicity than that of dimers linked by their carbon atoms in position C16 as described in FR 07/60 266.

The present invention also relates to 10-trifluoromethylartemisinin dimers in which only one of the endoperoxide bridges is reduced to an ether bridge, either on the C10 side, or on the C16 side. Indeed, "mono-endoperoxide" type dimers retain remarkable cytotoxic properties, and more particularly dimers in which the endoperoxide bridge on side $C_{16}$ has been reduced.

The present invention more particularly relates to a dimeric derivative of 10-trifluoromethylated artemisinin of formula (I):

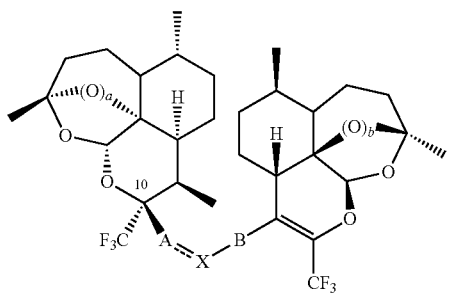

(I)

or a pharmaceutically acceptable salt thereof, wherein:
a and b represent, independently of each other, 1 or 2 but cannot represent 1 at the same time,
A represents:
   a heteroatom selected from an atom of nitrogen, oxygen and sulphur,
   the nitrogen atom being optionally substituted by a radical R1 selected from a hydrogen atom and the following groups: $(C_1-C_6)$alkyl, $(C_2-C_6)$alkenyl, $(C_2-C_6)$ alkynyl, $(C_3-C_8)$ cycloalkyl, aryl-$(C_1-C_6)$alkyl, heteroaryl-$(C_1-C_6)$alkyl, heterocycle-$(C_1-C_6)$alkyl, optionally substituted aryl, optionally substituted heteroaryl, —COR2, —CO$_2$R2, —C(O)NR2R2a, —SO$_2$R2, —CH$_2$C(O)OR2 and —CH$_2$C(O)NR2R2a,
   with R2 representing a hydrogen atom or one of the following groups: $(C_1-C_6)$alkyl, $(C_1-C_6)$ alkenyl, $(C_1-C_6)$ alkynyl, optionally substituted polyamine, $(C_3-C_8)$cycloalkyl, aryl-$(C_1-C_6)$alkyl, heteroaryl-$(C_1-C_6)$alkyl, optionally substituted aryl or optionally substituted heteroaryl, and
   R2a representing a hydrogen atom or a $(C_1-C_6)$alkyl group, or
   a saturated heterocycle comprising one or more heteroatoms selected from atoms of oxygen, sulphur and nitrogen, of which at least one nitrogen atom is linked to carbon 10,
----- represents a single bond when A represents an atom of oxygen or sulphur or a heterocycle, or represents a single bond or a double bond when A represents a nitrogen atom, the aforesaid nitrogen atom being substituted by a radical R1 as defined above when ----- represents a single bond,
B represents a —CH$_2$—Y—, —C(=O)—Y— or —CH (OR3)- group,
   with Y representing O, S, N—R1 or a heterocycle, with R1 as defined above, and R3 representing a hydrogen atom or a $(C_1-C_6)$alkyl or aryl group, and
X represents:
   when ----- represents a double bond:
      a =C(X1)-(O—X2)$_c$- group with X1 and X2 representing, independently of each other, a $(C_1-C_6)$alkyl or $(C_2-C_6)$ alkenyl group and c representing 0 or 1, or
   when ----- represents a single bond:
      one of the following groups: $(C_1-C_6)$alkyl optionally substituted by one or more OH groups; $(C_2-C_6)$ alkenyl; $(C_2-C_6)$alkynyl; $[(C_1-C_6)$alkyl$]_n$-$(C_2-C_2)$ cycloalkyl-$[(C_1-C_6)$alkyl$]_p$; $[(C_1-C_6)$alkyl$]_n$-heterocycle$[(C_1-C_6)$alkyl$]_p$; $[(C_1-C_6)$alkyl$]_n$-aryl-$[(C_1-C_6)$alkyl$]_p$; $[(C_1-C_6)$alkyl$]_n$-heteroaryl-$[(C_1-C_6)$alkyl$]_p$; with n and p representing, independently of each other, 0 or 1, a —CO—(CH$_2$)$_q$— or —CO—(CH$_2$)$_q$—CO— group for which q represents an integer equal to 1, 2, 3 or 4, or
a —CO$_r$—(CH$_2$)$_s$—Z—(CH$_2$)$_t$—CO$_u$— group for which r and u represent, independently of each other, an integer equal to 0 or 1,
s and t represent, independently of each other, an integer equal to 0, 1, 2, 3 or 4, and
Z represents an —S—, —S—S—, —SO—, —SO$_2$—, —Se—Se—, —O—P(O)(OR3)-O—, —NR1-, $(C_3-C_8)$-cycloalkyl, aryl or heteroaryl group, with R1 and R3 as defined above.

The dimeric derivatives of the present invention thus have the advantages of the fluorinated monomers recalled previously while exhibiting good antitumor properties.

In the present invention, "pharmaceutically acceptable" means that which is used for preparing a pharmaceutical composition that is generally safe, nontoxic and neither biologically nor otherwise undesirable and that is acceptable for veterinary use as well as for human pharmaceutical use.

In the present invention, "pharmaceutically acceptable salts" of a compound means salts that are pharmaceutically acceptable, as defined herein, and that have the desired pharmacological activity of the parent compound. Such salts include:
(1) hydrates and solvates,
(2) acid addition salts formed with inorganic acids such as hydrochloric acid, hydrobromic acid, sulphuric acid, nitric acid, phosphoric acid and similar; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and similar; and
(3) salts formed when an acid proton present in the parent compound is either replaced by a metal ion, for example an alkaline metal ion (Na$^+$, K$^+$ or Li$^+$ for example), an alkaline-earth metal ion (such as Ca$^{2+}$ or Mg$^{2+}$) or an aluminium ion; or coordinates with an organic or inorganic base. Acceptable organic bases include diethanolamine, ethanolamine, N-methylglucamine, triethanolamine, tromethamine and similar. Acceptable inorganic bases include aluminium hydroxide, calcium hydroxide, potassium hydroxide, sodium carbonate and sodium hydroxide.

"Halogen" means fluorine, bromine, chlorine or iodine. Preferably, it is fluorine, bromine or chlorine, more preferably fluorine.

In the context of the present invention, "$(C_1-C_6)$alkyl" group means a saturated, linear or branched hydrocarbon chain comprising from 1 to 6 carbon atoms, such as for example a methyl, ethyl, propyl, isopropyl, butyl, tert-butyl, pentyl or hexyl group. Depending on the case, this chain will be monovalent or bivalent. In the case of a bivalent chain, it will be advantageously a linear chain of formula —(CH$_2$)$_n$— where n represents an integer between 1 and 6 preferably equal to 1, 2, 3 or 4.

In the context of the present invention, "$(C_2-C_6)$alkenyl" group means an unsaturated, linear or branched hydrocarbon chain comprising from 1 to 6 carbon atoms, and comprising at least one double bond, and advantageously only one. It is notably a vinyl or allyl group. Depending on the case, this chain will be monovalent or bivalent. In the case of a bivalent chain, it will be advantageously a linear chain such as a chain of formula —CH$_2$—CH=CH—CH$_2$—.

In the context of the present invention, "(C$_2$-C$_6$)alkynyl" group means an unsaturated, linear or branched hydrocarbon chain comprising from 1 to 6 carbon atoms, and comprising at least one triple bond, and advantageously only one. It is notably an ethynyl or propynyl group. Depending on the case, this chain will be monovalent or bivalent. In the case of a bivalent chain, it will be advantageously a linear chain such as a chain of formula —CH$_2$—C≡C—.

In the context of the present invention, "polyamine" group means a linear hydrocarbon chain comprising from 6 to 20 carbon atoms, of which at least two of these carbon atoms are replaced by nitrogen atoms, two nitrogen atoms not being located on adjacent positions. The aforesaid polyamine group will be notably of the following formula:

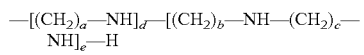

with a, b and c representing, independently of each other, an integer between 1 and 5 and d and e each representing 0 or 1.

Examples include a spermidine-type chain, i.e. of formula —(CH$_2$)$_4$—NH—(CH$_2$)$_3$—NH$_2$ or —(CH$_2$)$_3$—NH—(CH$_2$)$_4$—NH$_2$, a spermine-type chain of formula —(CH$_2$)$_3$—NH—(CH$_2$)$_4$—NH—(CH$_2$)$_3$—NH$_2$ or a chain of formula —(CH$_2$)$_4$—NH—(CH$_2$)$_4$—NH—(CH$_2$)$_4$—NH$_2$.

Said polyamine group can be optionally substituted, more particularly on the nitrogen atoms, notably by an N-protecting group such as (C$_1$-C$_6$)alkyl, (C$_2$-C$_6$) alkenyl, —CO—(C$_1$-C$_6$)alkyl, —CO—(C$_2$-C$_6$)alkenyl, —CO$_2$—(C$_1$-C$_6$)alkyl or —CO$_2$—(C$_2$-C$_6$)alkenyl.

The aforesaid optionally substituted polyamine group will thus be of the following general formula:

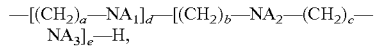

with a, b, c, d and e as defined above and A$_1$, A$_2$ and A$_3$, different or preferably identical, representing a hydrogen atom or an N-protecting group such as (C$_1$—C$_6$)alkyl, (C$_2$—C$_6$) alkenyl, —CO—(C$_1$—C$_6$)alkyl, —CO—(C$_2$—C$_6$) alkenyl, —CO$_2$—(C$_1$—C$_6$)alkyl or —CO$_2$—(C$_2$—C$_6$)alkenyl.

In the context of the present invention, "protecting group" means a group that selectively blocks a reactive site in a multifunctional compound in such a way that a chemical reaction can be carried out selectively at another unprotected reactive site as commonly defined in the field of chemical synthesis.

In the context of the present invention, "N-protecting group" means any substituent that protects the NH or NH$_2$ group against undesirable reactions such as the N-protecting groups described in Greene, "Protective Groups in Organic Synthesis", (John Wiley & Sons, New York (1981)) and Harrison et al. "Compendium of Synthetic Organic Methods", Vols. 1 to 8 (J. Wiley & Sons, 1971 to 1996). N-protecting groups include carbamates (such as —CO$_2$—(C$_1$—C$_6$)alkyl or —CO$_2$—(C$_2$—C$_6$)alkenyl), amides (such as —CO—(C$_1$-C$_6$)alkyl, —CO—(C$_2$—C$_6$)alkenyl), N-alkylated or N-alkenylated derivatives, amino acetal derivatives, N-benzylated derivatives, imine derivatives, enamine derivatives and N-heteroatom derivatives. In particular, the N-protecting group consists of formyl, acetyl, benzoyl, pivaloyl, phenylsulfonyl, benzyl (Bn), t-butyloxycarbonyl (Boc), benzyloxycarbonyl (Cbz), p-methoxybenzyloxycarbonyl, p-nitrobenzyl-oxycarbonyl, trichloroethoxycarbonyl (TROC), allyloxycarbonyl (Alloc), 9-fluorenylmethyloxycarbonyl (Fmoc), trifluoro-acetyl, benzyl carbamates (substituted or unsubstituted) and similar. It could be in particular a Boc group.

In the context of the present invention, "(C$_3$-C$_8$)-cycloalkyl" group means a saturated cyclic hydrocarbon group comprising from 3 to 8 carbon atoms, preferably 5 or 6 carbon atoms, for example a group such as cyclopropyl, cyclohexyl, cyclopentyl, etc. Depending on the case, this cycle will be monovalent or bivalent.

In the context of the present invention, "aryl" group means an aromatic group comprising preferably from 5 to 10 carbon atoms and comprising one or more joined rings, preferably 1 or 2 and more preferably only one, such as for example a phenyl or naphthyl group. Advantageously, it is a phenyl group. Depending on the case, this group will be monovalent or bivalent.

This aryl group can be optionally substituted, notably by one or more groups selected from a halogen atom and a (C$_1$-C$_6$)alkyl group as previously defined, an —OR, —NRR' and —SO$_2$R group with R and R' representing a hydrogen atom or a (C$_1$-C$_6$)alkyl group as previously defined.

In the context of the present invention, "heteroaryl nucleus" group means any aryl group as defined above in which one or more carbon atoms have been replaced by one or more heteroatoms, advantageously 1 to 4 and, even more advantageously 1 to 3, such as for example sulphur, nitrogen or oxygen atoms. Examples of heteroaryl groups include furyl, thienyl, pyrrolyl, pyridinyl, pyrimidinyl, pyrazolyl, imidazolyl, triazolyl, tetrazolyl or indyl groups. Advantageously, it is a pyridinyl or triazolyl group such as a 1,2,3-triazolyl. Depending on the case, this group will be monovalent or bivalent.

This heteroaryl group can optionally be substituted, notably by one or more groups selected from a halogen atom and a (C$_1$-C$_6$)alkyl group as previously defined, an —OR, —NRR' and —SO$_2$R group with R and R' representing a hydrogen atom or a (C$_1$-C$_6$)alkyl group as previously defined.

In the context of the present invention, "heterocycle" means a saturated, unsaturated or aromatic cyclic hydrocarbon compound, unless stated otherwise, comprising one or more joined rings, preferably 1 or 2 and more preferably only one, and comprising 5 to 10 cyclic atoms, of which one or more cyclic carbon atoms have been replaced by one or more heteroatoms, advantageously 1 to 4 and, even more advantageously 1 to 3, such as for example sulphur, nitrogen or oxygen atoms. It can be in particular a morpholinyl, piperazinyl, piperidinyl, furyl, thienyl, pyrrolyl, tetrazolyl or triazolyl group. Advantageously, it is a piperazinyl or triazolyl group such as a 1,2,3-triazolyl. Depending on the case, this group will be monovalent or bivalent.

If the heterocycle is saturated, it is advantageously a piperidine, morpholine or piperazine.

In the context of the present invention, "aryl-(C$_1$-C$_6$)alkyl" group means an aryl group as defined above linked to the molecule via a (C$_1$-C$_6$)alkyl group as defined above. It is in particular a benzyl group.

In the context of the present invention, "heteroaryl-(C$_1$-C$_6$) alkyl" group means a heteroaryl group as defined above linked to the molecule via a (C$_1$-C$_6$)alkyl group as defined above. It is in particular a benzyl group.

In the context of the present invention, "heterocycle-(C$_1$-C$_6$)alkyl" group means a heterocycle as defined above linked to the molecule via a (C$_1$-C$_6$)alkyl group as defined above. It is in particular a benzyl group.

Advantageously, a=b=2 or a=2 and b=1. More advantageously, a=b=2.

According to a particular embodiment of the invention, R1 represents a hydrogen atom, a ($C_1$-$C_6$)alkyl, ($C_2$-$C_6$) alkenyl, ($C_2$-$C_6$)alkynyl, ($C_3$-$C_8$)cycloalkyl, aryl-($C_1$-$C_6$)alkyl, heteroaryl-($C_1$-$C_6$)alkyl, heterocycle-($C_1$-$C_6$)alkyl, optionally substituted aryl, optionally substituted heteroaryl, —COR2, —$CO_2$R2, or —$SO_2$R2 group, with R2 representing a hydrogen atom or a ($C_1$-$C_6$)alkyl, ($C_3$-$C_8$)cycloalkyl, aryl-($C_1$-$C_6$)alkyl, heteroaryl-($C_1$-$C_6$) alkyl, optionally substituted aryl or optionally substituted heteroaryl group.

R1 can in particular represent a hydrogen atom.

Advantageously, R1 represents a hydrogen atom, a ($C_1$-$C_6$) alkyl, ($C_2$-$C_6$)alkenyl, —$CH_2$C(O)OR2 or —$CH_2$C(O)NR2R2a group, with R2 as previously defined and advantageously representing a hydrogen atom or an optionally substituted polyamine group, and R2a as previously defined and advantageously representing a hydrogen atom.

As indicated previously, B represents a —$CH_2$Y—, —C(=O)—Y— or —CH(OR3)- group, with Y and R3 as defined above. In the case of —$CH_2$Y— and —C(=O)—Y— groups, the carbon atom of these two groups is linked to the artemisinin nucleus whereas the Y group is linked to group X in general formula (I).

When Y represents a heterocycle, it is linked to the $CH_2$ or C(=O) group of radical B, preferably by a nitrogen atom.

Advantageously, B represents a —$CH_2$Y—, —C(=O)—Y— or —CH(OR3)- group, with Y representing O, NR1 or a heterocycle, with R1 and R3 as defined above and preferably each representing a hydrogen atom.

Preferably, B is selected from the groups —$CH_2$O—, —$CH_2$NR1-, —C(=O)NR1-, —CH(OR3)- and —$CH_2$-(heterocycle)-, with R1 and R3 as defined above, R3 advantageously representing a hydrogen atom and R1 advantageously representing a hydrogen atom, a ($C_1$-$C_6$)alkyl, ($C_2$-$C_6$) alkenyl, —$CH_2$C(O)OR2 or —$CH_2$C(O)NR2R2a group with R2 and R2a as defined above, R2 preferably representing a hydrogen atom or an optionally substituted polyamine chain and R2a preferably representing a hydrogen atom. In this case, R1 and R3 can more particularly each represent a hydrogen atom.

The heterocycle will be in particular, in this case, a heterocycle comprising only one ring of 5 or 6 members. Preferably, it will comprise one or more nitrogen atoms, preferably 1 to 4 nitrogen atoms, like a piperazinyl or triazolyl group such as 1,2,3-triazolyl.

B can represent in particular a —$CH_2$O—, —$CH_2$NH—, —CH(OH)—, —C(=O)NH—,

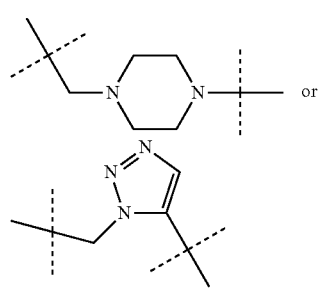

group. B can also represent a —$CH_2$N$CH_3$—, —$CH_2$N($CH_2$CH=$CH_2$)—, —$CH_2$N($CH_2$COOH)—, —$CH_2$N($CH_2$C(O)NH($CH_2$)$_3$NH($CH_2$)$_4$NH($CH_2$)$_3$NH$_2$)—, or

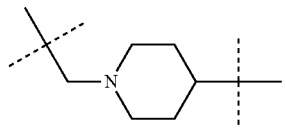

group.

Advantageously, B represents a —$CH_2$—Y— group with Y as defined above and preferably representing O, NR1 or a heterocycle, with R1 as previously defined.

Advantageously, A represents a nitrogen or oxygen atom. When A is linked to X by a single bond and represents a nitrogen atom, the nitrogen atom will preferably be substituted by a hydrogen atom.

Advantageously, A will represent an oxygen atom.

X can represent in particular, preferably when ----- represents a single bond:

a ($C_1$-$C_6$)alkyl, ($C_2$-$C_6$)alkenyl, ($C_2$-$C_6$)alkynyl, [($C_1$-$C_6$) alkyl]$_n$—($C_3$-$C_8$)cycloalkyl-[($C_1$-$C_6$)alkyl]$_p$, [($C_1$-$C_6$) alkyl]$_n$-heterocycle-[($C_1$-$C_6$)alkyl]$_p$, [($C_1$-$C_6$)alkyl]$_n$-aryl-[($C_1$-$C_6$)alkyl]$_p$ or [($C_1$-$C_6$)alkyl]$_n$-heteroaryl-[($C_1$-$C_6$)alkyl]$_p$ group, with n and p representing, independently of each other, 0 or 1, a —CO—($CH_2$)$_q$— or —CO—($CH_2$)$_q$—CO— group in which q represents an integer equal to 1, 2, 3 or 4, or a —CO$_r$($CH_2$)$_s$—Z—($CH_2$)$_t$—CO$_u$— group in which r and u represent, independently of each other, an integer equal to 0 or 1, s and t represent, independently of each other, an integer equal to 0, 1, 2, 3 or 4, and Z represents an —S, —S—S, —SO—, —SO$_2$—, —SeSe—, —O—P(O)(OR3)-O—, —NR1-, ($C_3$-$C_8$)cycloalkyl, aryl or heteroaryl group, with R1 and R3 as defined above.

According to a first particular embodiment, ----- represents a double bond and X represents a ($C_1$-$C_6$)alkyl, ($C_2$-$C_6$) alkenyl, ($C_2$-$C_6$)alkynyl, ($C_3$-$C_8$)cycloalkyl, or —X1-O—X2 group with X1 and X2 as defined above. In particular, X can represent a ($C_1$-$C_6$)alkyl, ($C_2$-$C_6$) alkenyl, ($C_2$-$C_6$) alkynyl or ($C_3$-$C_8$)cycloalkyl group, preferably a ($C_1$-$C_6$)alkyl group.

According to a second particular embodiment, ----- represents a single bond and X represents:

a ($C_1$-$C_6$)alkyl group optionally substituted by one or more OH groups; ($C_2$-$C_6$)alkenyl; ($C_2$-$C_6$)alkynyl; [($C_1$-$C_6$) alkyl]$_n$—($C_3$-$C_8$)cycloalkyl-[($C_1$-$C_6$)alkyl]$_p$; [($C_1$-$C_6$) alkyl]$_n$-heterocycle-[($C_1$-$C_6$)alkyl]$_p$; [($C_1$-$C_6$)alkyl]$_n$-aryl-[($C_1$-$C_6$)alkyl]$_p$; [($C_1$-$C_6$)alkyl]$_n$-heteroaryl-[($C_1$-$C_6$)alkyl]$_p$; with n and p representing, independently of each other, 0 or 1, or a —CO—($CH_2$)$_q$— or —CO—($CH_2$)$_q$—CO— group in which q represents an integer equal to 1, 2, 3 or 4, or optionally a —($CH_2$)$_q$—NR1- group with q representing an integer equal to 1, 2, 3 or 4 and R1 as defined above, R1 advantageously representing a —($C_1$-$C_6$)alkyl group such as methyl.

In this case, X will advantageously represent a ($C_1$-$C_6$) alkyl, ($C_2$-$C_6$)alkenyl, ($C_2$-$C_6$)alkynyl, [($C_1$-$C_6$)alkyl]$_n$-heteroaryl-[($C_1$-$C_6$)alkyl]$_p$, —($CH_2$)$_q$—NR1- or —CO—($CH_2$)$_q$— group, with n, p and q as defined above, preferably with n=p=1. The heteroaryl group will then be advantageously a heteroaryl comprising only one ring with 5 or 6 members and advantageously comprising one or more nitrogen atoms, preferably 1 to 3 nitrogen atoms.

In particular, X can represent a ($C_1$-$C_6$)alkyl, ($C_2$-$C_6$)alkenyl, ($C_2$-$C_6$)alkynyl, [($C_1$-$C_6$)alkyl]$_n$-heteroaryl-[($C_1$-$C_6$)alkyl]$_p$ or —CO—($CH_2$)$_q$— group, with n, p and q as defined above, preferably with n=p=1. The heteroaryl group will then be advantageously a heteroaryl comprising only one ring with 5 or 6 members and comprising advantageously one or more nitrogen atoms, preferably 1 to 3 nitrogen atoms.

In particular, X could be selected from the following groups: —(CH$_2$)$_n$— with n representing 1, 2, 3, 4, 5 or 6, —CH$_2$—CH(OH)—CH(OH)—CH$_2$—, —CH$_2$CH$_2$NCH$_3$—, —CO—CH$_2$—, —CH$_2$—CH═CH—CH$_2$—, —CH$_2$—C≡C—,

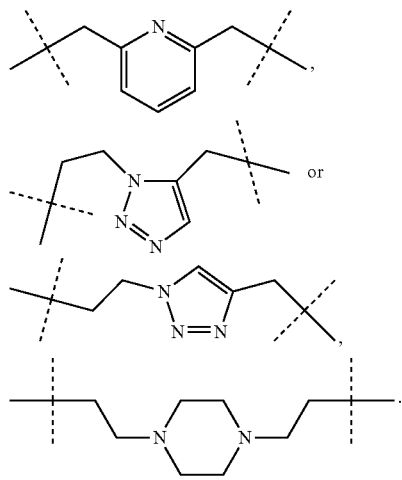

X could be notably selected from the following groups: —(CH$_2$)$_n$— with n representing 1, 2, 3 or 4, —CO—CH$_2$—, —CH$_2$—CH═CH—CH$_2$—, —CH$_2$—C≡C—,

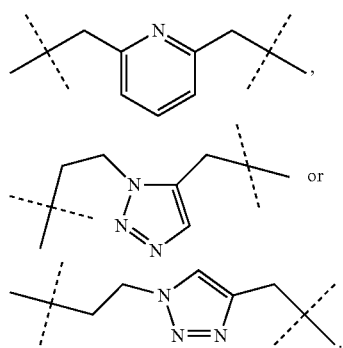

According to a particular embodiment of the invention, the compounds of the invention correspond to compounds of formula (I) wherein:
a, b and ----- are as previously defined,
A represents a heteroatom selected from an oxygen or nitrogen atom, the nitrogen atom being substituted by a hydrogen atom when ----- represents a single bond,
B represents a —CH$_2$—Y—, —C(═O)—NH— or —CH(OH)— group, with Y representing O, N—R1 or a heterocycle, R1 being selected from a hydrogen atom, a (C$_1$-C$_6$)alkyl, (C$_2$-C$_6$)alkenyl, —CH$_2$C(O)OR2 and —CH$_2$C(O)NHR2 group, with R2 representing a hydrogen atom, or an optionally substituted polyamine group, and
X represents:
  when ----- represents a double bond: a ═C(X1)-(O—X2)$_c$- group with X1 and X2 representing, independently of each other, a (C$_1$-C$_6$)alkyl or (C$_2$-C$_6$)alkenyl group and c representing 0 or 1, or
  when ----- represents a single bond:
    a (C$_1$-C$_6$)alkyl group optionally substituted by one or more OH groups; (C$_2$-C$_6$)alkenyl; (C$_2$-C$_6$)alkynyl; [(C$_1$-C$_6$)alkyl]$_n$-heterocycle-[(C$_1$-C$_6$)alkyl]$_p$; [(C$_1$-C$_6$)alkyl]$_n$-heteroaryl-[(C$_1$-C$_6$)alkyl]$_p$; with n and p representing, independently of each other, 0 or 1,
    a —CO—(CH$_2$)$_q$— group in which q represents an integer equal to 1, 2, 3 or 4, or
    a —(CH$_2$)$_q$—NR4 group in which q represents an integer equal to 1, 2, 3 or 4 with R4 representing a hydrogen atom or a (C$_1$-C$_6$)alkyl group.

According to another particular embodiment of the invention, the inventive compounds of the invention correspond to compounds of formula (I) wherein:
a and b are as previously defined,
----- represents a single bond,
A represents an oxygen atom,
B represents a —CH$_2$—Y— group, with representing O, N—R1 or a heterocycle, R1 being as previously defined and advantageously representing a hydrogen atom, a (C$_1$-C$_6$)alkyl, (C$_2$-C$_6$)alkenyl, —CH$_2$C(O)OR2 or —CH$_2$C(O)NR2R2a group,
with R2 as previously defined and advantageously representing a hydrogen atom or an optionally substituted polyamine group, and R2a as previously defined and advantageously representing a hydrogen atom, and
X represents a (C$_1$-C$_6$)alkyl, (C$_2$-C$_6$)alkenyl, (C$_2$-C$_6$)alkynyl, [(C$_1$-C$_6$)alkyl]$_n$-heterocycle-[(C$_1$-C$_6$)alkyl]$_p$, or [(C$_1$-C$_6$)alkyl]$_n$-heteroaryl-[(C$_1$-C$_6$)alkyl]$_p$ group, with n and p representing, independently of each other, 0 or 1.

The compounds of the invention of formula (I) could be selected more particularly among the following compounds:

1

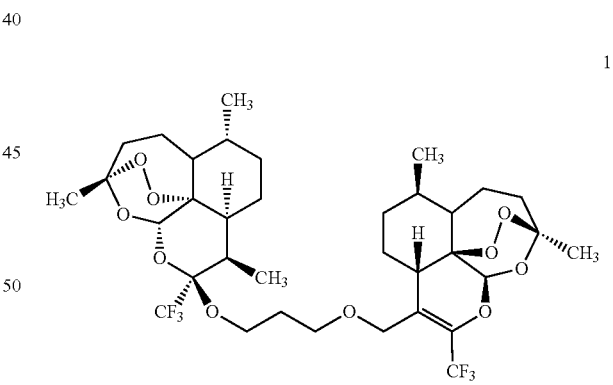

2

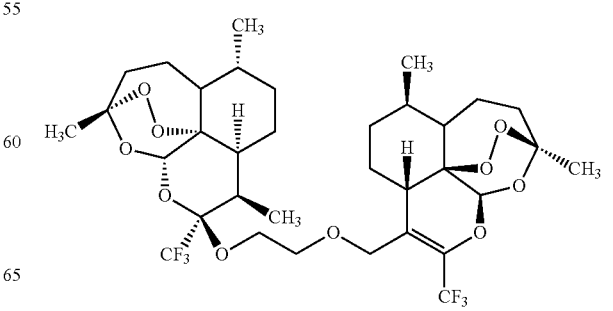

3
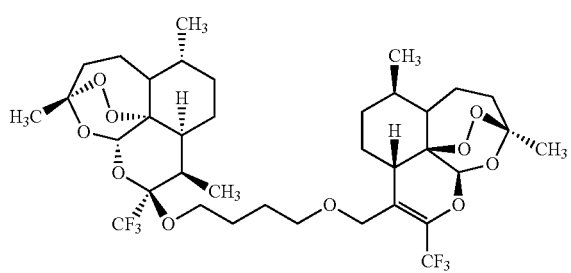
4
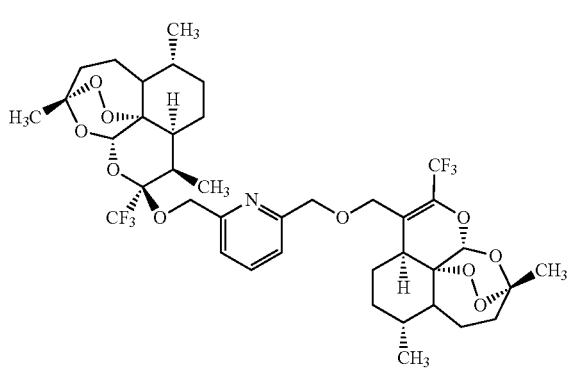
5
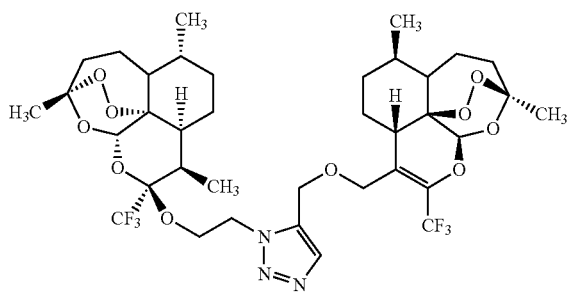
6
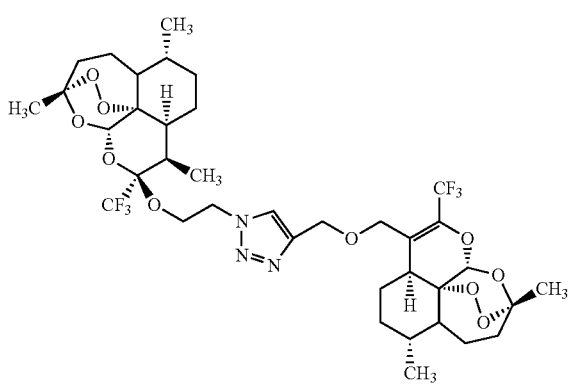
7
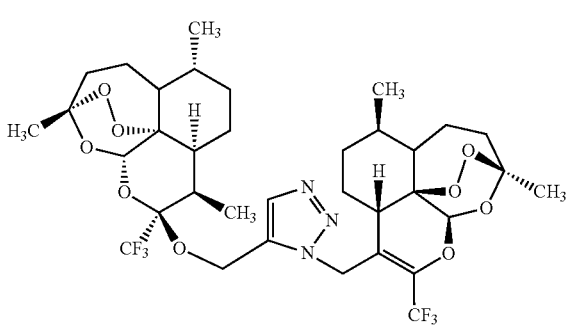
8
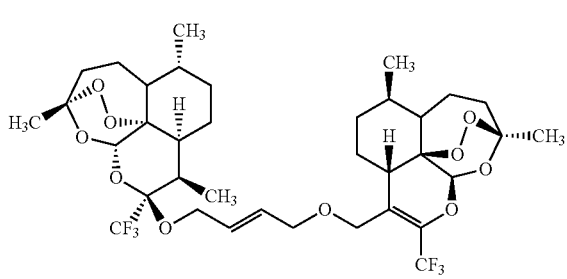
9
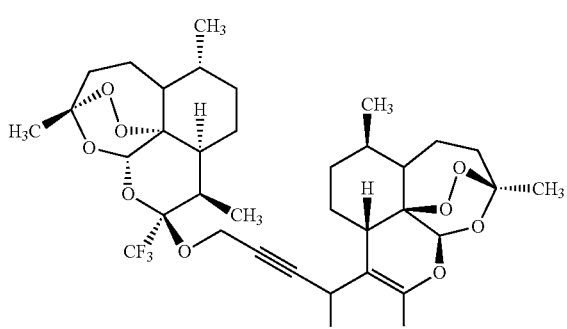
10
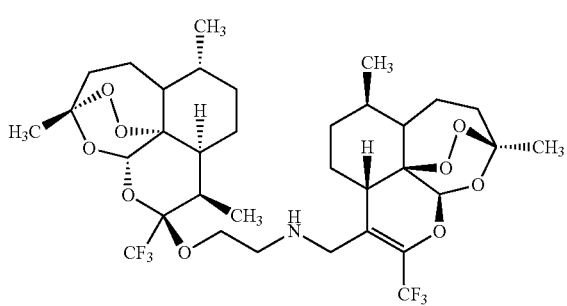
11
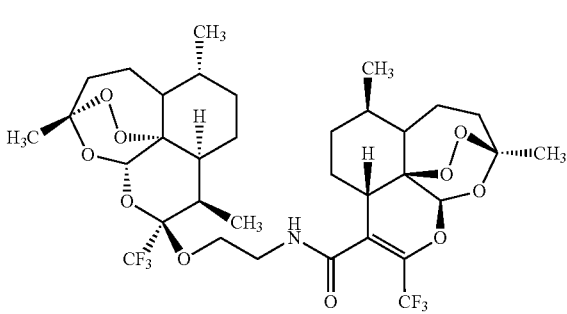

12
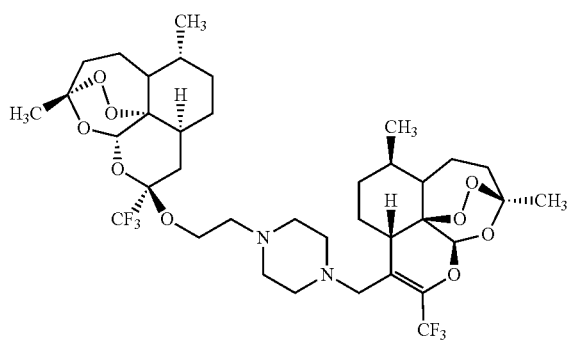
13
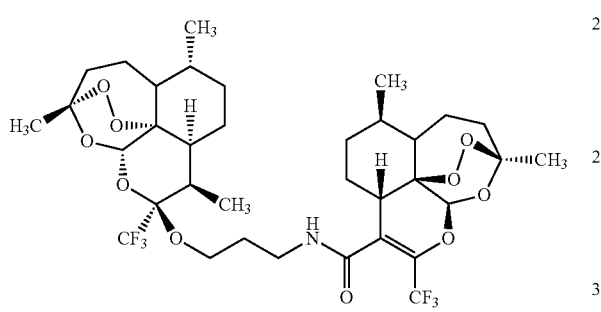
14
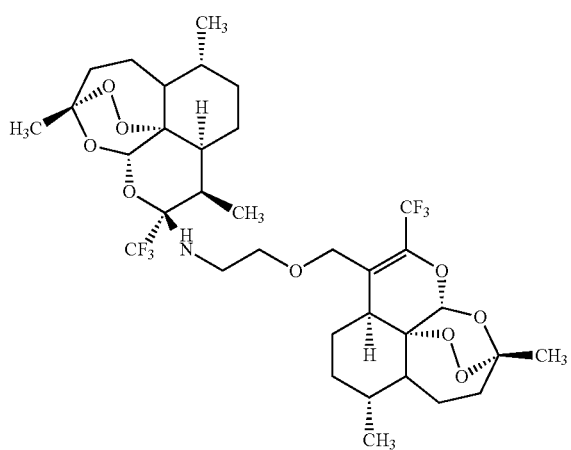
15
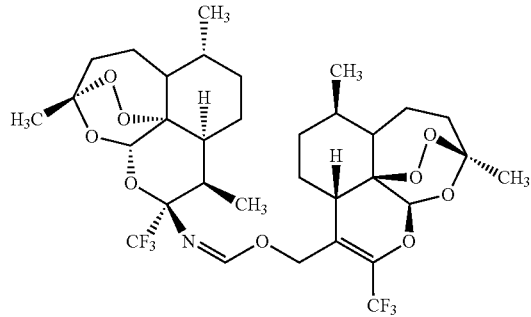
16
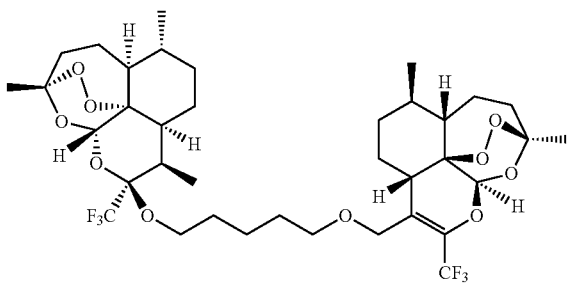
17
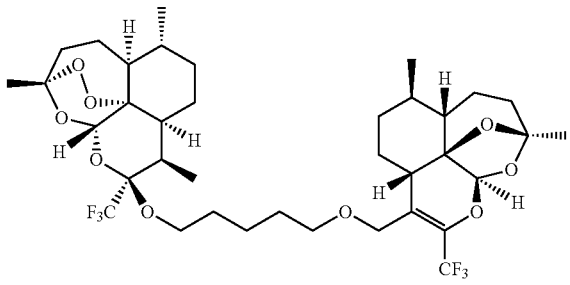
18
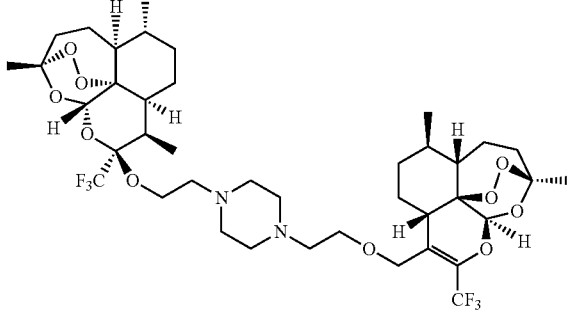
19
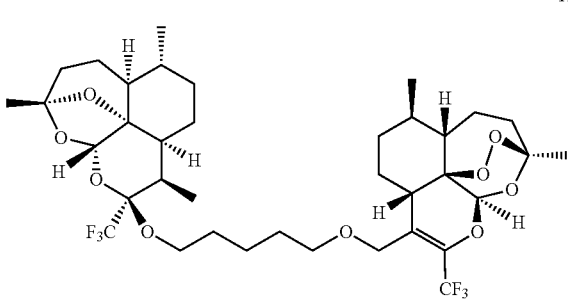
20
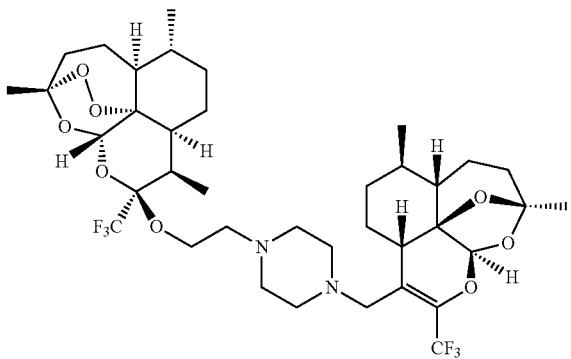

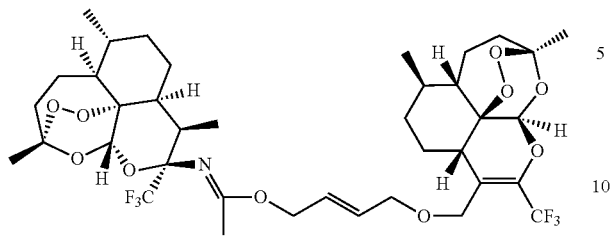
21
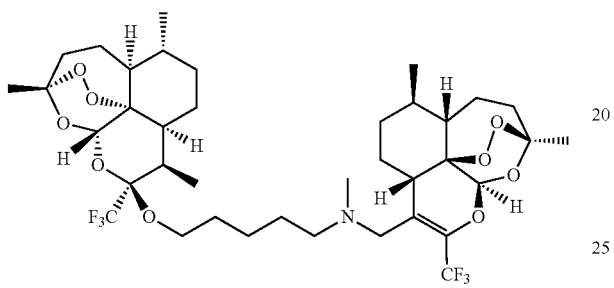
22
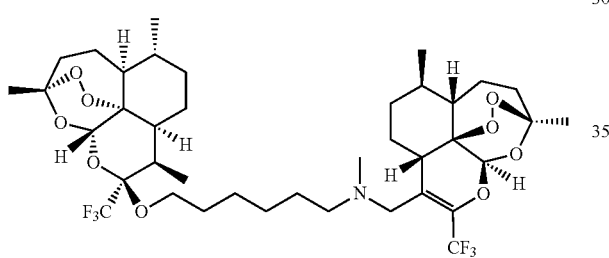
23
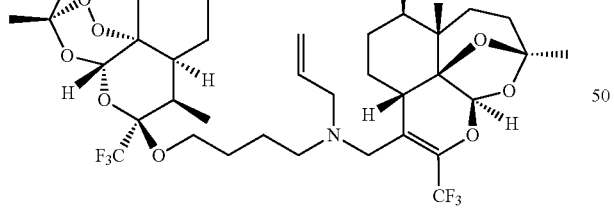
24
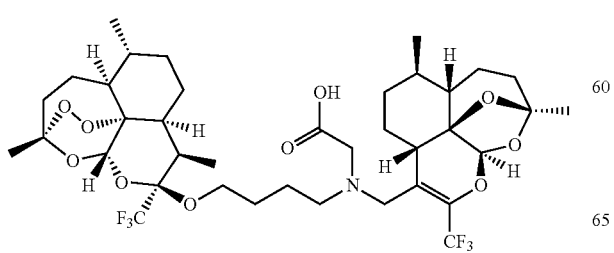
25
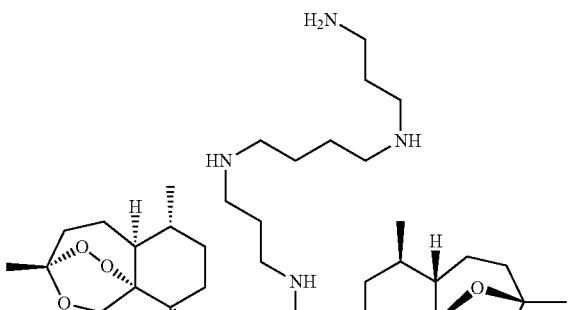
26
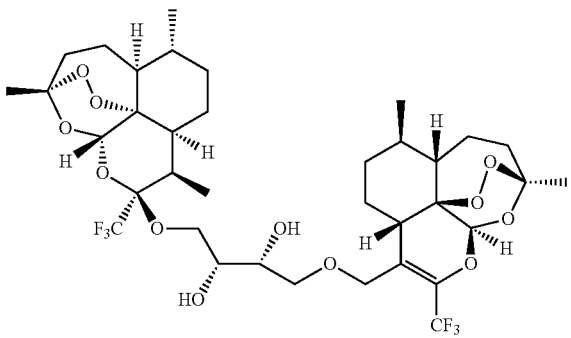
27
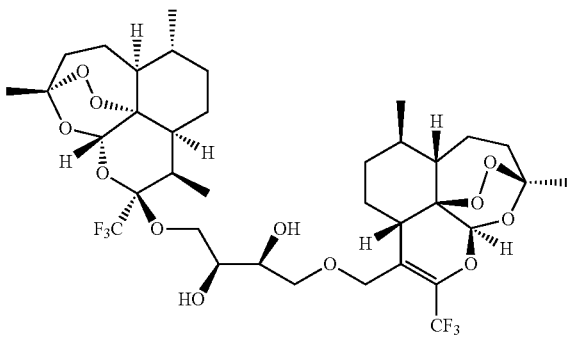
28
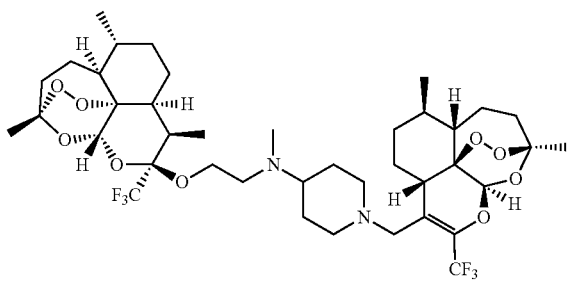
29

The present invention also relates to a compound of formula (I) as defined above for the use thereof as a drug, notably for treating cancer.

The invention also relates to the use of a compound of the invention for manufacturing a drug for treating cancer.

The invention further relates to a method for treating cancer, comprising the administration of an effective quantity of at least one compound of formula (I) as defined above to a patient in need thereof.

The present invention also relates to a pharmaceutical composition comprising at least one compound according to the invention and at least one pharmaceutically acceptable carrier.

The compounds of the invention can be administered by oral, sublingual, parenteral, subcutaneous, intramuscular, intravenous, transdermal, local or rectal route, preferably by oral, intravenous or subcutaneous route.

In the pharmaceutical compositions of the present invention for oral, sublingual, parenteral, subcutaneous, intramuscular, intravenous, transdermal, local or rectal administration, the active ingredient can be administered in unit dosage forms, in mixture with traditional pharmaceutical carriers, to animals or humans. Suitable unit dosage forms comprise forms by oral route such as tablets, gelatine capsules, powders, granules and oral solutions or suspensions; sublingual and oral administration forms; parenteral, subcutaneous, intramuscular, intravenous, intranasal or intraocular administration forms; and forms for rectal administration.

When a solid composition in tablet form is prepared, the principal active ingredient is mixed with a pharmaceutical carrier such as gelatine, starch, lactose, magnesium stearate, talc, gum arabic or analogues. Tablets can be coated with saccharose or other suitable materials or can be treated in such a way that they have extended or delayed activity and that they continuously release a predetermined quantity of active ingredient.

A preparation in gelatine capsules is obtained by mixing the active ingredient with a diluent and by pouring the mixture obtained into soft or hard gelatine capsules.

A preparation in syrup or elixir form can contain the active ingredient together with a sweetener, an antiseptic, as well as a flavouring agent and a suitable colorant.

Water-dispersible powders or granules can contain the active ingredient in mixture with dispersion or wetting agents, or suspension agents, as well as with flavour correctors or sweeteners.

For rectal administration, suppositories that are prepared with binders that melt at rectal temperature, for example cocoa butter or polyethylene glycols, are used.

For parenteral, intranasal or intraocular administration, aqueous suspensions, isotonic saline solutions or sterile and injectable solutions that contain pharmacologically compatible dispersants and/or wetting agents are used.

The active ingredient can also be formulated in the form of microcapsules, optionally with one or more additives.

The compounds of the invention can be used in doses between 0.01 mg and 1,000 mg per day, and can be given in a single dose once per day or can be administered in several doses throughout the day, for example twice a day in equal doses. The daily dose administered is advantageously between 5 mg and 500 mg, even more advantageously between 10 mg and 200 mg. It may be necessary to use doses beyond these ranges according to the experience of the person skilled in the art.

In a particular embodiment, this composition can further include at least one other active ingredient, advantageously selected from anticancer agents.

Nonrestrictive examples of anticancer agents include 6-mercaptopurine, fludarabine, cladribine, pentostatin, cytarabine, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocin, carboplatin, cisplatin, oxaliplatin, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrozole, letrozole, tamoxifen, octreotide and lanreotide.

The present invention also relates to a pharmaceutical composition comprising:
  (i) at least one compound of formula (I) as defined above, and
  (ii) at least one other active ingredient, notably used for treating cancer,
as combination products for a simultaneous, separated or sequential use.

Nonrestrictive examples of active ingredient include 6-mercaptopurine, fludarabine, cladribine, pentostatin, cytarabine, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocin, carboplatin, cisplatin, oxaliplatin, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrozole, letrozole, tamoxifen, octreotide or lanreotide.

The pharmaceutical composition as described above can be used in particular for treating cancer.

The present invention also relates to the use of a pharmaceutical composition comprising:
  (i) at least one compound of formula (I) as defined above, and
  (ii) at least one other active ingredient, notably used for treating cancer,
as combination products for a simultaneous, separated or sequential use, for manufacturing a drug for treating cancer.

The compounds of the invention can be prepared notably from intermediates A, $A_1$, B, C, D, E, F, G, $G_1$ and R described below. Thus, the compounds of the invention are obtained by a coupling between intermediate G, $G_1$, or R and intermediate A, $A_1$, B, C, D, E or F, coupling that can be carried out in one or more steps.

Intermediates A and B:

Synthesis of intermediate A, artemisinin bromo-trifluoromethyl, and hydroxylated derivative B are described in *J. Med. Chem.*, 47, 1423-33, (2004) and WO 03/035 651. The protocol is indicated in the reaction mechanism below.

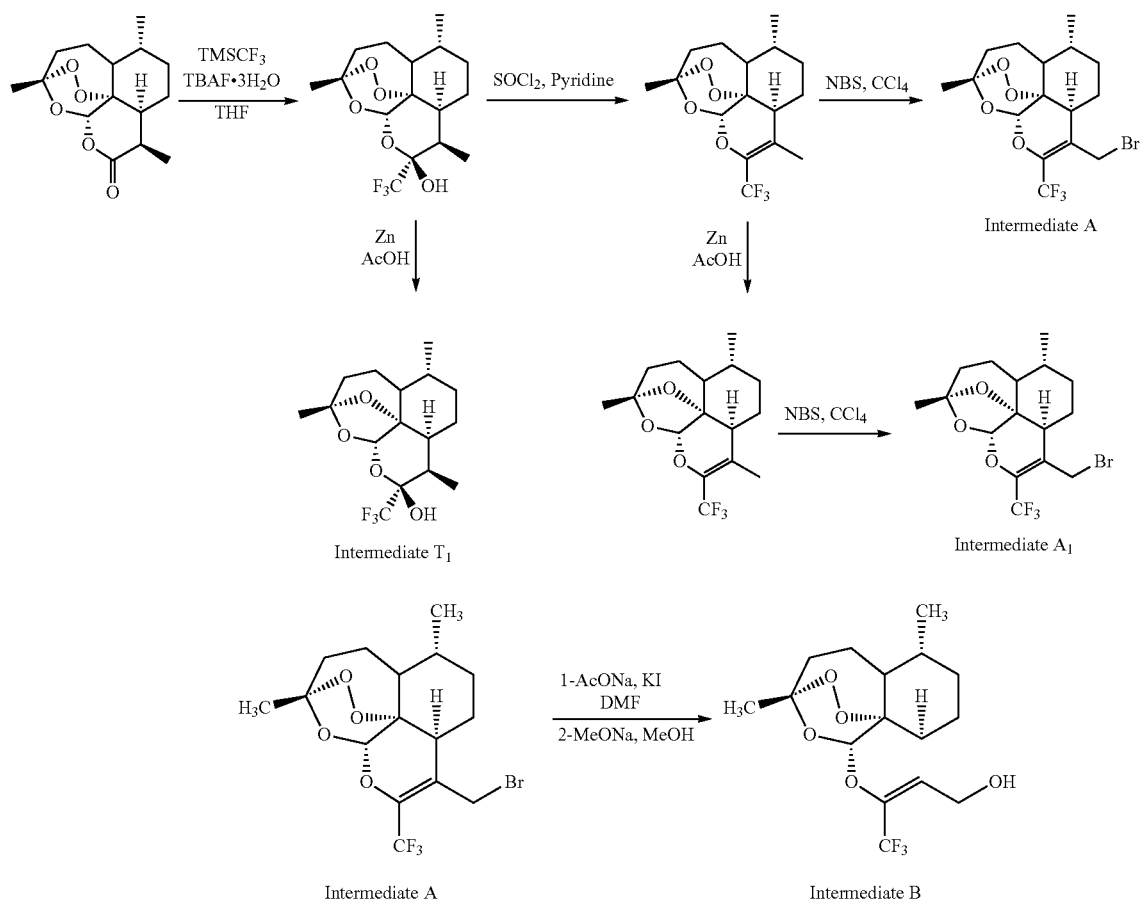

(TMS=trimethylsilyl; TBAF=tetrabutylammonium fluoride; THF=tetrahydrofuran; NBS=N-bromosuccinimide; Ac=acetyl; Me=methyl; DMF=dimethylformamide)

Intermediates C and D:

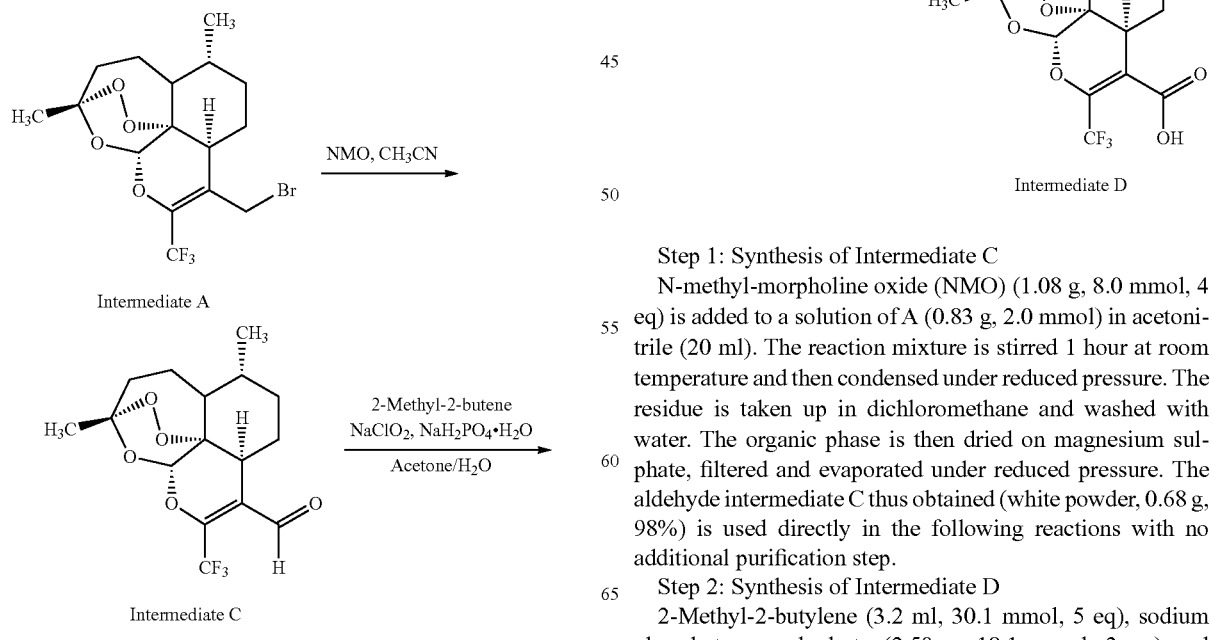

Step 1: Synthesis of Intermediate C

N-methyl-morpholine oxide (NMO) (1.08 g, 8.0 mmol, 4 eq) is added to a solution of A (0.83 g, 2.0 mmol) in acetonitrile (20 ml). The reaction mixture is stirred 1 hour at room temperature and then condensed under reduced pressure. The residue is taken up in dichloromethane and washed with water. The organic phase is then dried on magnesium sulphate, filtered and evaporated under reduced pressure. The aldehyde intermediate C thus obtained (white powder, 0.68 g, 98%) is used directly in the following reactions with no additional purification step.

Step 2: Synthesis of Intermediate D

2-Methyl-2-butylene (3.2 ml, 30.1 mmol, 5 eq), sodium phosphate monohydrate (2.50 g, 18.1 mmol, 3 eq) and sodium chlorite (1.64 g, 18.1 mmol, 3 eq) are successively added to a solution of intermediate C (2.10 g, 6.0 mmol) in an acetone/water mixture (1.5/1, 75 ml). The reaction mixture is stirred 18 hours at room temperature and then condensed under reduced pressure. After dilution with ethyl acetate, the organic phase is washed with water and then with saturated sodium chloride solution, and dried on magnesium sulphate. After filtering, the solvents are evaporated under reduced pressure. The residue is purified by silica gel chromatography (80:20 cyclohexane/ethyl acetate); intermediate D is isolated with a yield of 54% (white powder, 1.2 g).

Intermediates E and F:

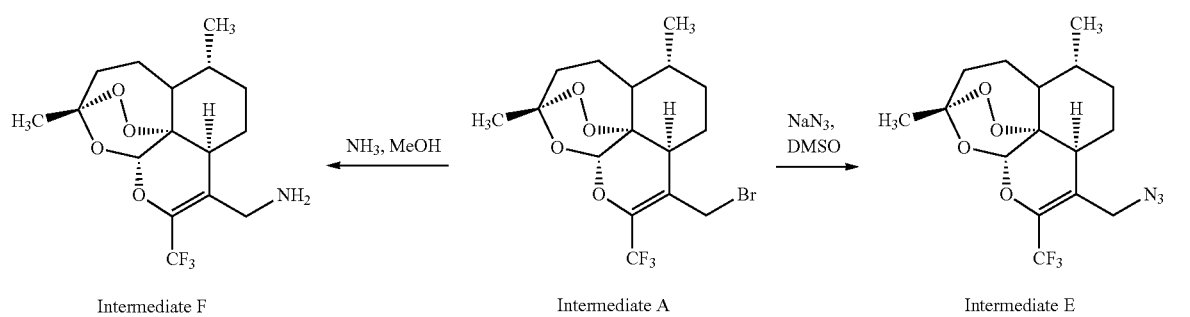

Synthesis of Intermediate E:

Sodium azide (0.14 g, 2.25 mmol, 1.5 eq) is added to a solution of intermediate A (0.63 g, 2.5 mmol) in dimethyl sulfoxide (DMSO) (10 ml). The reaction mixture is stirred at room temperature for 1.5 hours. It is then poured into water and the extraction is carried out in ethyl acetate. The organic phase is dried on magnesium sulphate, filtered and the solvents are evaporated under reduced pressure. The azide intermediate E thus obtained (white powder, 0.56 g, 100%) is used directly in the following reactions with no additional purification step.

Synthesis of Intermediate F:

Intermediate A (1.03 g, 2.5 mmol) is dissolved in an ammonia solution in methanol (7 N, 10 ml). The reaction mixture is stirred at room temperature for 3 hours and then evaporated under reduced pressure. The residue is purified by silica gel chromatography (95:5 and then 90:10 dichloromethane/methanol); intermediate F is isolated with a yield of 59% (pale yellow powder, 0.52 g).

Intermediates G and R:

The synthesis of intermediate G necessary to the preparation of the compounds of the invention is described in *Org. Lett.*, 4, 757-759, (2002), whose protocol is indicated on the reaction mechanism below.

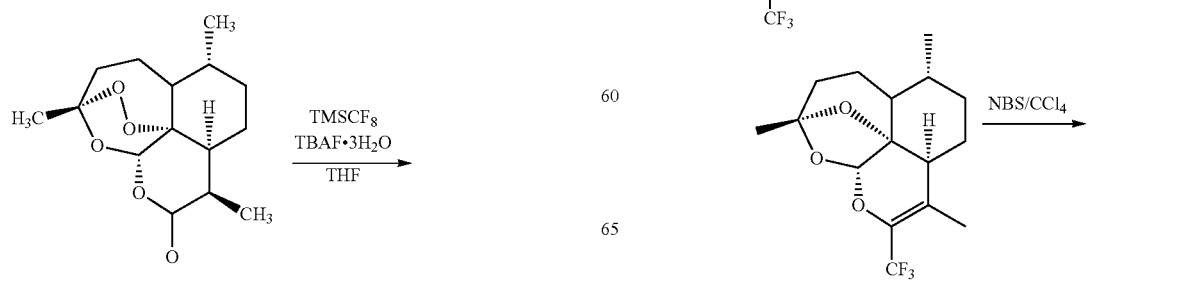

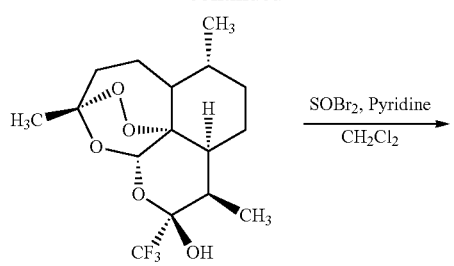

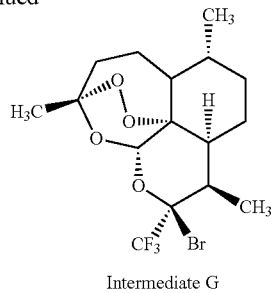

Synthesis of intermediate R from intermediate G is described in the synthesis process for compound 14 below.

Intermediates $A_1$ and $G_1$:

Intermediates $A_1$ and $G_1$ have a reduced endoperoxide bridge in the artemisinin nucleus.

Synthesis of Intermediate $A_1$:

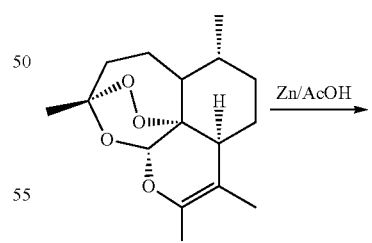

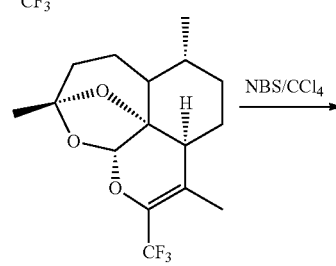

-continued

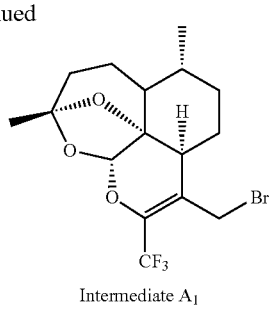

Intermediate A₁

Zinc powder (264 mg, 0.403 mmol, 4.5 eq) is added to a solution of the trifluoromethyl derivative described in *J. Med. Chem.*, 47, 1423-33, (2004) (300 mg, 0.897 mmol) in 100% acetic acid (8 ml). After 4.5 hours of stirring at room temperature, the reaction medium is filtered on silica and then concentrated under reduced pressure. The crude reaction product is purified by silica gel chromatography with an eluent gradient (100:0 to 90:10 petroleum ether/diethyl ether). The reduced-bridge derivative is obtained with a yield of 90% (259 mg).

N-bromosuccinimide (NBS) (290 mg, 1.62 mmol, 2 eq) is added to a solution of the reduced-bridge derivative (259 mg, 0.813 mmol) in carbon tetrachloride (10 ml). The reaction medium is instantaneously carried to reflux. After 1 hour at this temperature, the reaction mixture is diluted with dichloromethane (5 ml), washed with saturated NaHCO₃ solution (2×5 ml) and then with saturated NaCl solution (5 ml). The organic phase is dried on MgSO₄, filtered and concentrated under reduced pressure. The crude reaction product is purified by silica gel chromatography with an eluent gradient (100:0 to 90:10 petroleum ether/diethyl ether). Intermediate A₁ is obtained with a yield of 60% (186 mg).

Synthesis of Intermediate G₁:

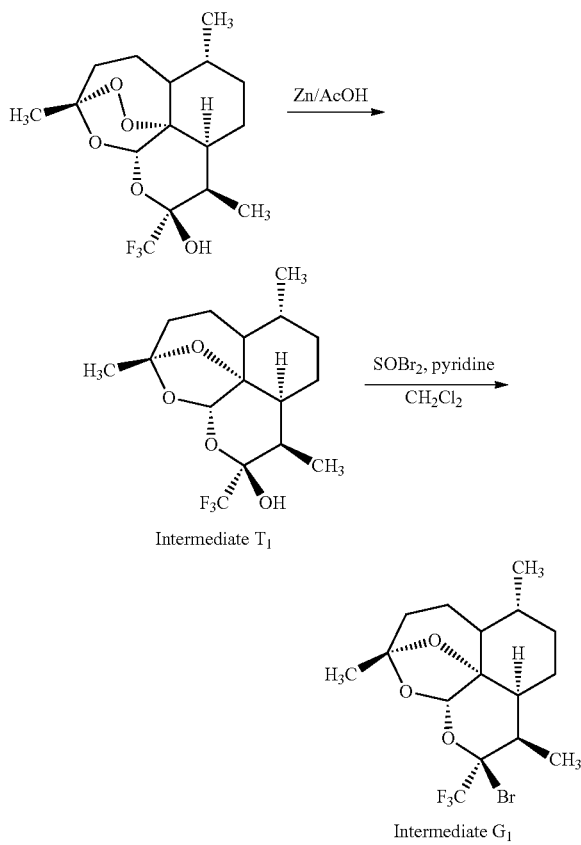

Zinc powder (1.25 g, 19.15 mmol, 4.5 eq) is added to a trifluoromethyl alcohol solution described in *J. Med. Chem.*, 47, 1423-33, (2004) (1.5 g, 4.25 mmol) in 100% acetic acid (37.5 ml). After 4.5 hours of stirring at room temperature, the reaction medium is filtered on silica and then concentrated under reduced pressure. Reduced-bridge intermediate T₁ is obtained with a quantitative yield (1.42 g).

The latter (1.42 g, 4.23 mmol) is dissolved in dichloromethane (26 ml), to which are added, at 0° C. and successively: pyridine (690 µl, 8.46 mmol, 2 eq) and then thionyl bromide (972 µl, 8.46 mmol, 2 eq). The reaction mixture is allowed to return to room temperature and after 4.5 hours of stirring is hydrolyzed with saturated NaCl solution. The organic phase is basified with saturated NaHCO₃ solution (2×10 ml), washed with saturated NaCl solution (10 ml), dried on MgSO₄, filtered and concentrated under reduced pressure. Intermediate G₁ is obtained with a yield of 80% (1.34 g).

The present invention thus relates to a method for preparing a compound of formula (I) as defined above, wherein the compound of formula (I) is obtained by coupling a compound of following formula (II):

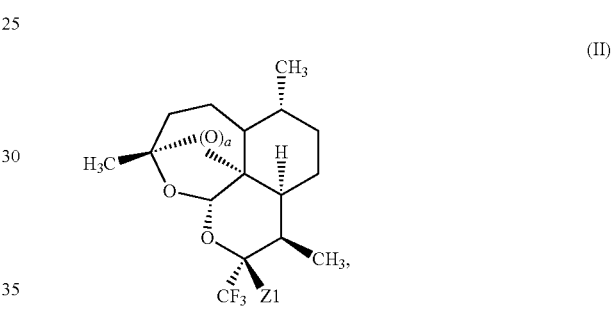

(II)

wherein a is as previously defined and Z1 represents a halogen atom, preferably a bromine atom, or an —OH, —NH₂ or —NHR1 group, with R1 as defined above, preferably Z1 representing a halogen atom or an —OH or —NH₂ group, with a compound of following formula (III):

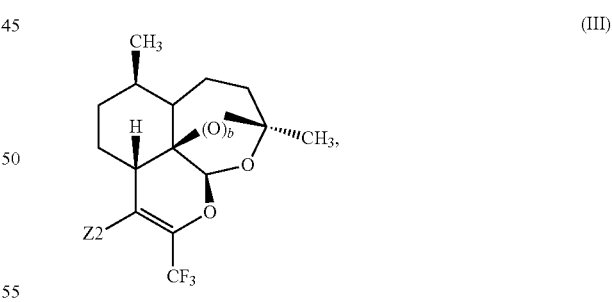

(III)

wherein b is as previously defined and Z2 represents a —CH₂OH, —CHO, —COOH, —CH₂N₃, —CH₂NH₂ or —CH₂Hal group, where Hal represents a halogen atom, preferably a bromine atom.

The compound of formula (I) thus obtained could be separated from the reaction medium by methods well known to those persons skilled in the art, such as for example by extraction, solvent evaporation or by precipitation and filtering.

The compound could in addition be purified if necessary by techniques well known to those persons skilled in the art, such as by recrystallization if the compound is crystalline, by distillation, by silica gel column chromatography or by high-performance liquid chromatography (HPLC).

Coupling can comprise one or more reaction steps carried out by techniques well known to those persons skilled in the art.

According to a first particular embodiment, a compound of formula (I) wherein B=—CH$_2$Y— or —C(=O)—Y—, with Y as defined above, can be prepared by coupling between compounds (II) and (III) and a compound of following formula (IV):

$$Z3-X-Z4 \qquad (IV),$$

with:

X as defined above,

Z3 representing a halogen atom, such as a bromine or chlorine atom, or an —OH, —NHR1, —SH, —N$_3$, —C(=O)R4 group or a heterocycle comprising at least one intracyclic NH group, with R1 as defined above and R4 representing a hydrogen atom or a (C$_1$-C$_6$)alkyl group, and Z4 representing a halogen atom, such as a bromine or chlorine atom, or an —OH, —NHR1, —SH, —N$_3$ group or a heterocycle comprising at least one intracyclic NH group, with R1 as defined above.

In this case, the Z2 function carried by the compound of formula (III) will be preferably a —CH$_2$OH, —CH$_2$NH$_2$ or —CH$_2$Hal group (to give access to compounds (I) with B=—CH$_2$O—, —CH$_2$NR1- or —CH$_2$S—) or —COOH group (to give access to compounds (I) with B=—C(=O)O—, —C(=O)NR1- or —C(=O)S—), and more preferably a —CH Hal or —COOH group.

In the case where Z3 and/or Z4 represent a heterocycle, the active function that will react in the coupling Step will obviously be the intracyclic NH group. The heterocycle will preferably have 5 or 6 members, such as a morpholinyl, piperidinyl or piperazinyl group.

The compound of formula (I) is then obtained in two steps, (1) by coupling the Z1 function of compound (II) with the Z3 function of compound (IV), and (2) by coupling the Z2 function of compound (III) with the Z4 function of compound (IV). These two steps (1) and (2) can be carried out in any order using techniques well known to the person skilled in the art.

If necessary, function Z3 or Z4, which must not react in the first coupling step, could be protected beforehand and then deprotected once this Step is carried out. Notably, if a free amine function (NH$_2$) is desired, it could be obtained from the halogenated derivative or from an azide (N$_3$). An amine function (NH or NH$_2$) could also be protected in carbamate form, notably by a Boc group. Similarly, a halogen atom could be obtained by halogenation of an OH group (for example in the presence of N-bromosuccinimide to obtain a bromine atom).

Similarly, it can be necessary to activate certain functions that play a part in coupling (Z1, Z2, Z3 or Z4). Notably, an acid function (COOH) can be activated in the form of an acyl chloride (COCl).

Additional functionalisation steps can also be carried out (see Examples 25 and 26).

The compound of formula (IV) could either be commercial or be prepared by methods well known to the person skilled in the art.

According to a first aspect, Z3 represents a halogen atom, a heterocycle or an —OH, —NHR1, —SH or —N$_3$ group, which gives access to compounds of formula (I) in which ----- represents a single bond.

According to a second aspect, Z3 represents a —C(=O)R4 group and Z1 represents an —NH$_2$ group, which gives access to compounds of formula (I) in which ----- represents a double bond and thus A represents a nitrogen atom.

This first particular embodiment of the method for preparing the compounds of the invention is illustrated notably with the synthesis of compounds 1, 2, 3, 4, 10, 11, 12, 13, 14, 16, 17, 18, 19, 20, 22, 23, 24, 25, 26 and 29.

According to a second particular embodiment, a compound of formula (I) wherein B=—CH(OR3)-, with R3 as defined above, can be prepared by coupling between compounds (II) and (III), with Z2=—CHO, and a compound of following formula (V):

$$Z5-X-Z6 \qquad (V),$$

with:

X as defined above,

Z5 representing a halogen atom, such as a bromine or chlorine atom, or an —OH, —NHR1, —SH, —N$_3$ or —C(=O)R4 group or a heterocycle comprising at least one intracyclic NH group, with R1 and R4 as defined above, and Z6 representing an acid hydrogen atom or a halogen atom.

In the context of the present invention "acid hydrogen atom" means a hydrogen atom that can be displaced by a base. One such acid hydrogen atom can be in particular an acetylenic hydrogen atom.

In the case where Z5 represents a heterocycle, the active function that will react in the coupling Step will obviously be the intracyclic NH group. The heterocycle will preferably have 5 or 6 members, such as a morpholinyl, piperidinyl or piperazinyl group.

This method will comprise in particular the following successive steps:

(i) reaction of compound (V) with compound (II) to yield following compound (VI):

(VI)

[Chemical structure with CH$_3$, H$_3$C, (O)$_a$, O, CF$_3$, A, X, Z6 groups]

with a, A, X and Z6 as previously defined, (ii) formation, from compound (VI) obtained in preceding Step (I), of the following organometallic compound (VII):

(VII)

[Chemical structure with CH$_3$, H$_3$C, (O)$_b$, O, CF$_3$, A, X, M groups]

with b, A and X as previously defined and M representing an alkaline metal such as lithium or an alkaline-earth metal halide such as magnesium chloride or bromide, (iii) reaction of compound (VII) obtained in preceding Step (ii) with a compound of formula (III) wherein Z2=—CHO to yield a compound of formula (I) in which B=—CH(OH)—, (iv) optionally substitution of the hydroxyl function of the compound of formula (I) obtained in preceding Step (iii) to yield a compound of formula (I) in which B=—CH(OR3)- with R3≠H, and (v) separation from the reaction medium of the compound of formula (I) obtained in Step (iv) or (v).

Organometallic compound (VII) can be formed from compound (VI) in which Z6=H by reaction with an organometallic base such as an alkyllithium (like n-Bu-Li) or an alkylmagnesium bromide or chloride.

When compound (VI) includes a Z6 group representing a halogen atom such as a bromine atom, halogen-metal exchange can give access to desired compound (VII) by reaction of compound (VI) with a metal such as lithium or magnesium.

The compound of formula (V) could either be commercial or be prepared by methods well known to the person skilled in the art.

According to a first aspect, Z5 represents a halogen atom, a heterocycle or an —OH, —NHR1, —SH or —N$_3$ group, which gives access to compounds of formula (I) in which ----- represents a single bond. In this case, Z5 preferably represents an —OH, —NHR1 or —SH group and Z1 represent a halogen atom such as a bromine atom.

According to a second aspect, Z5 represents a —C(=O)R4 group and Z1 represents an —NH$_2$ group, which gives access to compounds of formula (I) in which ----- represents a double bond and thus A represents a nitrogen atom.

This second particular embodiment of the method for preparing the compounds of the invention is notably illustrated with the synthesis of compound 9.

According to a third particular embodiment, coupling is carried out by cross-metathesis of alkenes or alkynes as illustrated with the preparation of compounds 8 and 21. In this case, one or more preliminary steps must be carried out to introduce a group carrying a terminal double or triple bond in place of the Z1 and Z2 groups of compounds (II) and (III).

Moreover, additional functionalisation steps can be carried out, notably steps that functionalize the double or triple bond formed during metathesis (see Examples 27 and 28).

Thus, a compound of formula (I) wherein: ----- represents a single bond, A represents a heteroatom, B=—CH$_2$O—, —CH$_2$NR1- or —CH$_2$S— and X=—(CH$_2$)$_y$—Z7-(CH$_2$)$_z$—, with Z7 representing a —CH=CH— or —C≡C— group and y and z representing, independently of each other, an integer between 0 and 4, with y+z≤4, or ----- represents a double bond, A represents N, B=—CH$_2$O—, —CH$_2$NR1- or —CH$_2$S— and X represents =C((C$_1$-C$_6$)alkyl)-O—(CH$_2$)$_y$—Z7-(CH$_2$)$_z$—, with Z7, y and z as defined above,
can be obtained by a cross-metathesis reaction between the compound of following formula (VIII):

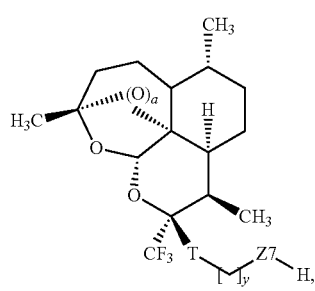

(VIII)

with a, Z7 and y as previously defined, and T representing A or —N=C((C$_1$-C$_6$)alkyl)-O—, and the compound of following formula (IX):

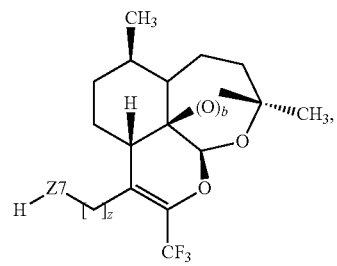

(IX)

with b, B, Z7 and z as previously defined.

This reaction will be carried out in the presence of a metathesis catalyst such as a 1$^{st}$ or 2$^{nd}$ generation Grubbs' catalyst.

Preferably, Z7 represents a —CH=CH— group.

Compound (VIII) could be prepared by reaction of a compound of formula (II), wherein Z1 preferably represents a halogen atom, with a compound of formula Z7-(CH$_2$)$_y$—R, where Z7 and y are as defined above and R represents an OH, NHR1 or SH group, with R1 as defined above.

Compound (IX) could be prepared by reaction of a compound of formula (III), wherein Z2 preferably represents a halogen atom, with a compound of formula Z7-(CH$_2$)$_z$—R', where Z7 and z are as defined above and R' represents an OH, NHR1 or SH group, with R1 as defined above.

According to a fourth particular embodiment, coupling is carried out by a [4+2] or [3+2] cycloaddition reaction, as illustrated with the preparation of compounds 5, 6 and 7. In this case, one or more preliminary steps must be carried out to introduce suitable groups in place of the Z1 and Z2 groups of compounds (II) and (III), like an alkene or an alkyne for one of the two groups and a diene or a 1,3-dipole such as an N$_3$ group for the other group.

According to a fifth particular embodiment, a compound of formula (I) wherein -A-X-B- represents —N=C((C$_1$-C$_5$)alkyl)-O—CH$_2$— can be prepared by coupling in basic medium a compound of formula (III) in which Z2 represents a halogen atom such as a bromine atom with a compound of following formula (X):

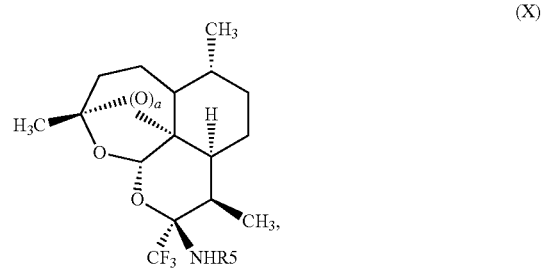

(X)

with a as defined above and R5 representing an acyl group of formula —C(=O)—(C$_1$-C$_5$)alkyl.

Preferably, this reaction is carried out in the presence of NaH as base, notably in the presence of KI.

The compound of formula (X) can be prepared by acylation starting with a compound of formula (II) wherein Z1=NH$_2$ or according to the protocol described for the synthesis of intermediate V.

This second particular embodiment of the method for preparing the compounds of the invention is notably illustrated with the synthesis of compound 15.

In all the methods described above, additional substitution and/or activation and/or protection/deprotection steps, well known to the person skilled in the art, could be carried out if necessary.

The present invention will be better understood in the light of the nonrestrictive examples which follow.

EXAMPLES

Example 1

Synthesis of the of the Invention Compounds

Synthesis of Compounds 1, 2, 3, 4, 16, 17, 18 and 19

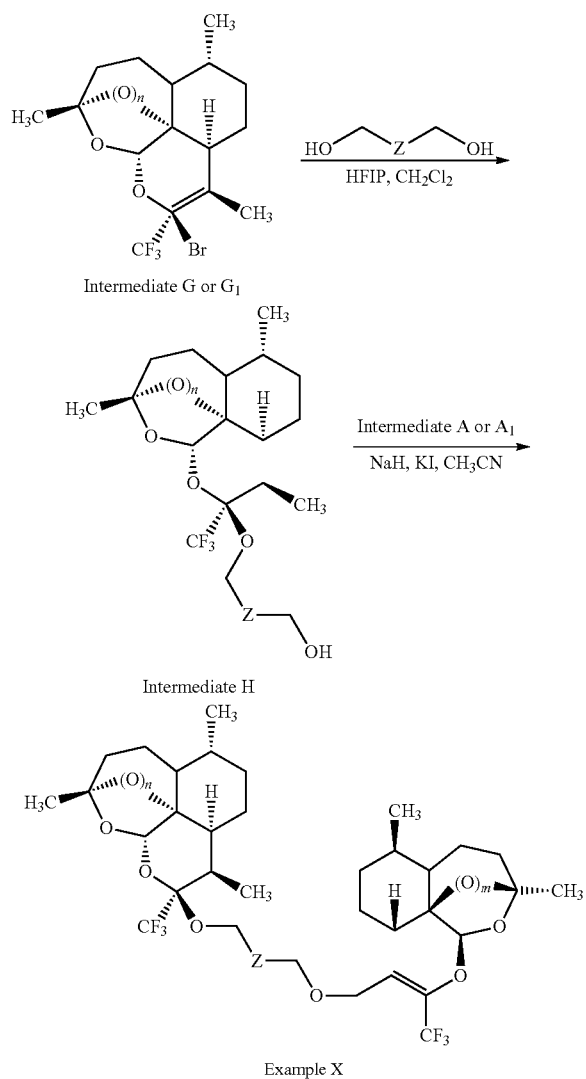

(Z represents a single bond or a —$CH_2$—, —$(CH_2)_2$—, —$(CH_2)_3$—, pyridinyl or

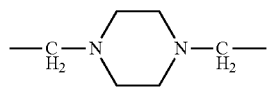

group in Examples 1 to 4 and 16 to 19)

General Method A:

Step 1: Diol (HO—$CH_2$—Z—$CH_2$OH) (10 eq) and hexafluoroisopropanol (HFIP) (5 eq) are successively added to a solution of intermediate G or $G_1$ (1 eq) in dichloromethane (c=0.14). The reaction mixture is then stirred at room temperature for 5 hours before dilution with dichloromethane. The organic phase is washed with sodium hydrogen carbonate solution and dried on magnesium sulphate. After filtering, the solvents are evaporated under reduced pressure. The crude product obtained is purified by silica gel chromatography (cyclohexane/ethyl acetate) to yield intermediate $H_x$.

Intermediate $H_1$: obtained with a yield of 71% in the form of a white powder from 1,3-propanediol and intermediate G (85:15 to 70:30 cyclohexane/ethyl acetate).

Intermediate $H_2$: obtained with a yield of 71% in the form of a white powder from 1,2-ethanediol and intermediate G (90:10 cyclohexane/ethyl acetate).

Intermediate $H_3$: obtained with a yield of 25% in the form of a translucent oil from 1,4-butanediol and intermediate G (80:20 cyclohexane/ethyl acetate).

Intermediate $H_4$: obtained with a yield of 39% in the form of a translucent oil from 2,6-pyridinedimethanol and intermediate G (95:5 to 75:25 cyclohexane/ethyl acetate).

Intermediate $H_5$: obtained with a yield of 82% in the form of a colourless oil from 1,5-pentanediol and intermediate G (100 to 80:20 cyclohexane/ethyl acetate).

Intermediate $H_6$: obtained with a yield of 61% in the form of a yellow oil from 1,6-hexanediol and intermediate G (95:5 to 80:20 cyclohexane/ethyl acetate).

Intermediate $H_7$: obtained with a yield of 49% in the form of a yellow foam from 1,4-bis-(2-hydroxyethyl)piperazine and intermediate G (100:0 to 90:10 dichloromethane/methanol).

Intermediate $H_8$: obtained with a yield of 22% in the form of an oil from 1,5-pentanediol and intermediate $G_1$ (100:0 to 60:40 cyclohexane/ethyl acetate).

Step 2: Intermediate $H_x$ (1 eq) is added to a NaH suspension (60% in oil, 2.5 eq) in acetonitrile (or dimethyl sulfoxide) (c=0.1); after 10 minutes of stirring, a solution of intermediate A or $A_1$ (1.25 eq) in acetonitrile (or in dimethyl sulfoxide) (c=0.1) and potassium iodide (in catalytic quantity) is added to this mixture. The reaction medium is stirred at room temperature for 1 to 5 hours before dilution in ethyl acetate. The organic phase is washed with sodium hydrogen carbonate solution and dried on magnesium sulphate. After filtering, the solvents are evaporated under reduced pressure. The crude product obtained is purified by silica gel chromatography (cyclohexane/ethyl acetate) to lead to the expected dimer.

Example 1 obtained with a yield of 45% in the form of a white powder from intermediate $H_1$ and intermediate A (95:5 to 70:30 cyclohexane/ethyl acetate).

Example 2 obtained with a yield of 40% in the form of a white powder from intermediate $H_2$ and intermediate A (90:10 cyclohexane/ethyl acetate).

Example 3 obtained with a yield of 20% in the form of a white powder from intermediate $H_3$ and intermediate A (95:5 cyclohexane/ethyl acetate).

Example 4 obtained with a yield of 30% in the form of a white powder from intermediate $H_4$ and intermediate A (95:5 to 90:10 cyclohexane/ethyl acetate).

Example 16 obtained with a yield of 45% in the form of a white powder from intermediate H$_5$ and intermediate A (85:15 cyclohexane/ethyl acetate).

Example 17 obtained with a yield of 40% in the form of a white powder from intermediate H$_6$ and intermediate A$_1$ (75:2 cyclohexane/ethyl acetate).

Example 18 obtained with a yield of 58% in the form of a white powder from intermediate H$_7$ and intermediate A (97:3 dichloromethane/methanol).

Example 19 obtained with a yield of 1% in the form of a colorless oil from intermediate H$_8$ and intermediate A (98:2 to 70:30 cyclohexane/ethyl acetate).

Synthesis of Compounds 5 and 6
Synthesis of Intermediate J:

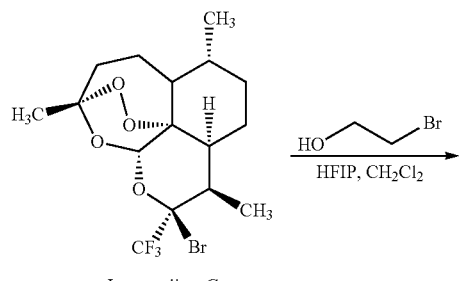

Intermediate G

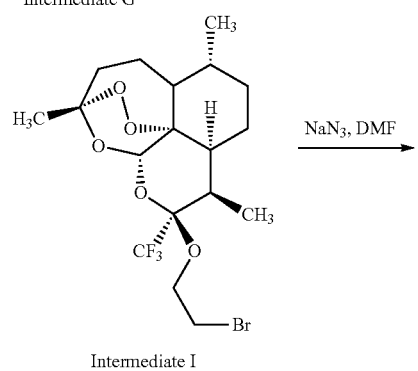

Intermediate I

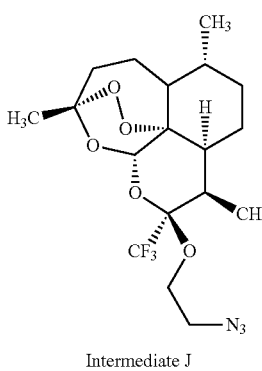

Intermediate J

Step 1: 2-Bromo-ethanol (1.41 ml, 20.0 mmol, 10 eq) and hexafluoroisopropanol (1.05 ml, 10.0 mmol, 5 eq) are successively added to a solution of intermediate G (0.83 g, 2.0 mmol) in dichloromethane (14 ml). The reaction mixture is then stirred at room temperature for 2 hours before dilution with dichloromethane. The organic phase is washed with sodium hydrogen carbonate solution and then dried on magnesium sulphate. After filtering, the solvents are evaporated under reduced pressure. The crude product obtained is purified by silica gel chromatography (95:5 cyclohexane/ethyl acetate); intermediate I is isolated with a yield of 40% (pale yellow powder, 0.365 g).

Step 2: Sodium azide (0.02 g, 0.3 mmol, 2 eq) is added to a solution of intermediate I (0.07 g, 0.15 mmol) in dimethyl sulfoxide (2 ml). The reaction mixture is stirred at room temperature for 1 hour. After dilution with ethyl acetate, the organic phase is washed with water and then dried on magnesium sulphate. After filtering, the solvents are evaporated under reduced pressure and intermediate J obtained quantitatively is used directly in the following step (white powder).

Synthesis of Intermediate K:

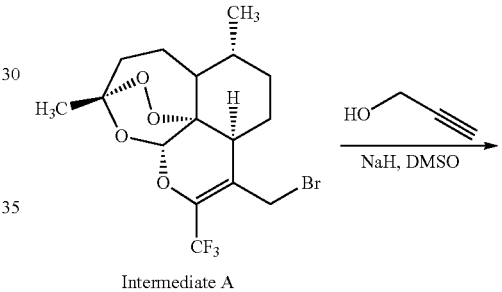

Intermediate A

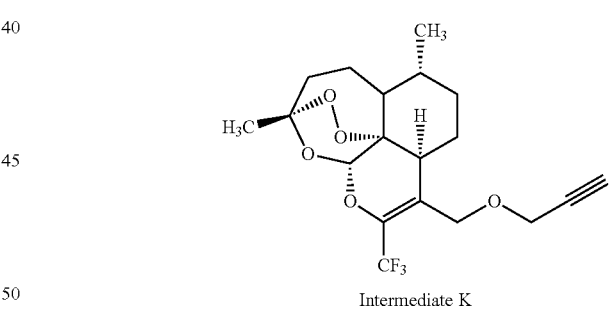

Intermediate K

Propargyl alcohol (64 µl, 1.0 mmol, 1 eq) is added to an NaH (60% in oil, 0.04 g, 1.0 mmol, 1 eq) suspension in dimethyl sulfoxide (DMSO) (4 ml); after 5 minutes of stirring, a solution of intermediate A (0.41 g, 1.0 mmol) in dimethyl sulfoxide (2 ml) is added to this mixture. The reaction medium is stirred at room temperature for 1.5 hours before dilution with ethyl acetate. The organic phase is washed with sodium hydrogen carbonate solution and then dried on magnesium sulphate. After filtering, the solvents are evaporated under reduced pressure. The crude product obtained is purified by silica gel chromatography (95:5 cyclohexane/ethyl acetate); intermediate K is isolated with a yield of 80% (colorless oil, 0.31 g).

Coupling of Intermediates J and K:

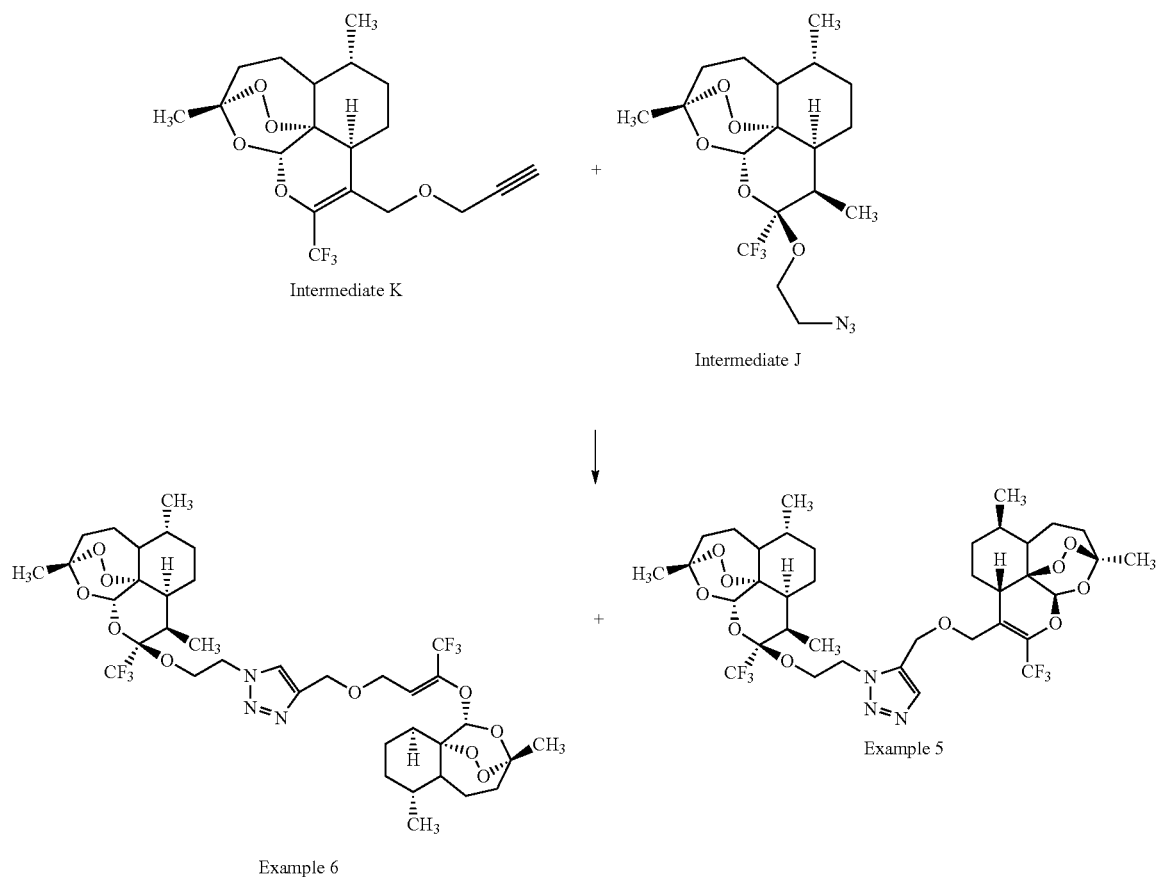

A mixture of intermediate J (0.063 g, 0.15 mmol, 1 eq) and intermediate K (0.062 g, 0.15 mmol, 1 eq) are heated at 90° C. for 4 hours in a sealed tube. After returning to room temperature, the reaction medium is purified by silica gel chromatography (90:10 to 75:25 cyclohexane/ethyl acetate); compound 5, less polar, and compound 6 are isolated with a total yield of 68% (white powder, 0.035 g and 0.048 g, respectively).

Synthesis of Compound 7

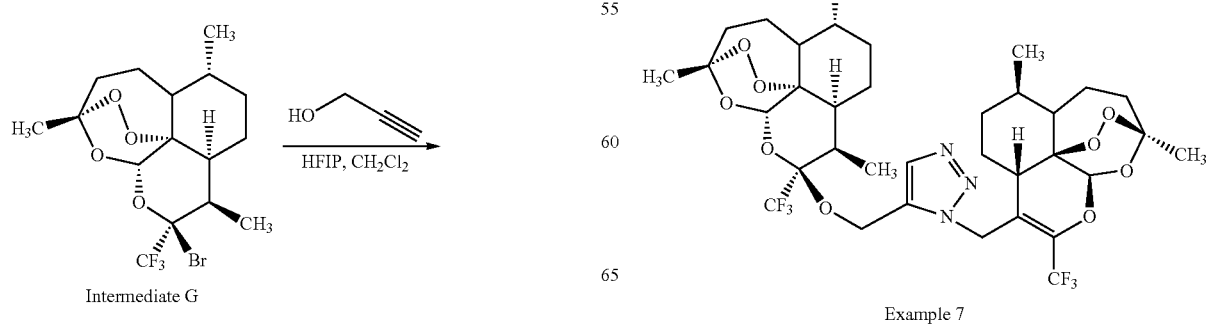

Step 1: Propargyl alcohol (295 μl, 5.0 mmol, 10 eq) and hexafluoroisopropanol (HFIP) (263 μl, 2.5 mmol, 5 eq) are successively added to a solution of intermediate G (0.207 g, 0.5 mmol) in dichloromethane (3.5 ml). The reaction mixture is then stirred at room temperature for 2 hours before dilution with dichloromethane. The organic phase is washed with sodium hydrogen carbonate solution and dried on magnesium sulphate. After filtering, the solvents are evaporated under reduced pressure. The crude product obtained is purified by silica gel chromatography (97:3 cyclohexane/ethyl acetate); intermediate L is isolated with a yield of 68% (white powder, 0.133 g).

Step 2: A mixture of intermediate E (0.056 g, 0.15 mmol, 1 eq) and intermediate L (0.058 g, 0.15 mmol, 1 eq) is heated at 90° C. for 16 hours in a sealed tube. After returning to room temperature, the reaction medium is purified by silica gel chromatography (80:20 cyclohexane/ethyl acetate); compound 7 is isolated with a total yield of 28% (white powder, 0.032 g).

Synthesis of Compound 8

Synthesis of Intermediate M:

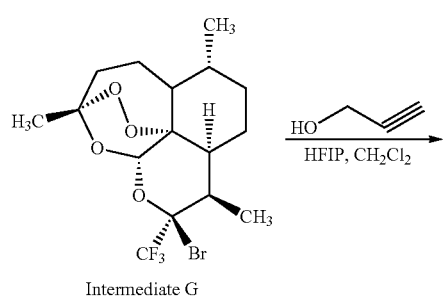

Intermediate G

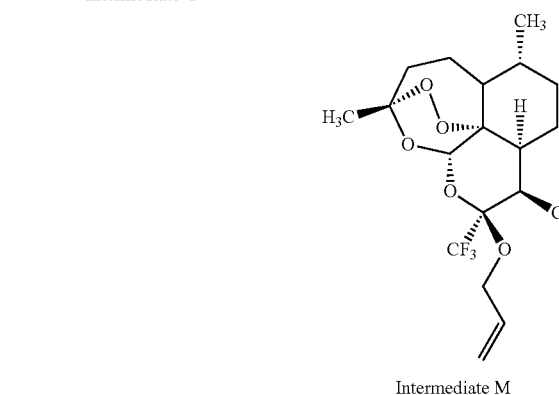

Intermediate M

Allyl alcohol (823 μl, 12.0 mmol, 10 eq) and hexafluoroisopropanol (634 μl, 6.0 mmol, 5 eq) are successively added to a solution of intermediate G (0.5 g, 1.2 mmol) in dichloromethane (7 ml). The reaction mixture is then stirred at room temperature for 4 hours before dilution with dichloromethane. The organic phase is washed with sodium hydrogen carbonate solution and dried on magnesium sulphate. After filtering, the solvents are evaporated under reduced pressure. The crude product obtained is purified by silica gel chromatography (95:5 cyclohexane/ethyl acetate); intermediate M is isolated with a quantitative yield (white powder, 0.47 g).

Synthesis of Intermediate N:

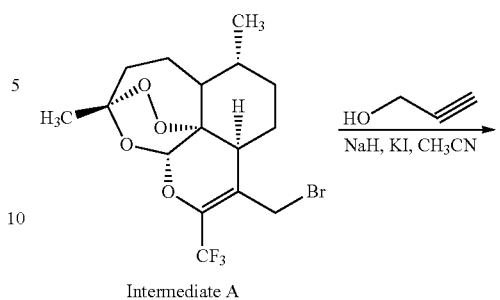

Intermediate A

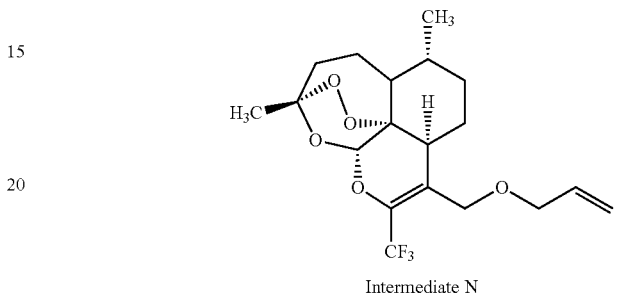

Intermediate N

Allyl alcohol (60 μl, 0.87 mmol) is added to an NaH (60% in oil, 0.11 g, 2.72 mmol, 2.5 eq) suspension in acetonitrile (2 ml); after 5 minutes of stirring, a solution of intermediate A (0.45 g, 1.1 mmol, 1.25 eq) in acetonitrile (2 ml) and potassium iodide (in catalytic quantity) is added to this mixture. The reaction medium is stirred at room temperature for 16 hours before dilution with ethyl acetate. The organic phase is washed with sodium hydrogen carbonate solution and dried on magnesium sulphate. After filtering, the solvents are evaporated under reduced pressure. The crude product obtained is purified by silica gel chromatography (95:5 to 90:10 cyclohexane/ethyl acetate); intermediate N is isolated with a yield of 34% (white powder, 0.15 g).

Coupling of Intermediates M and N:

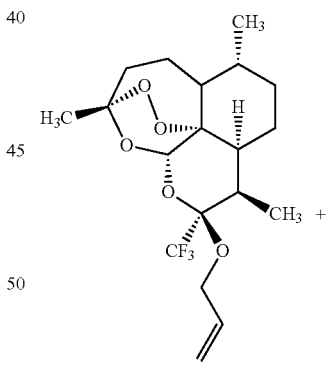

Intermediate M

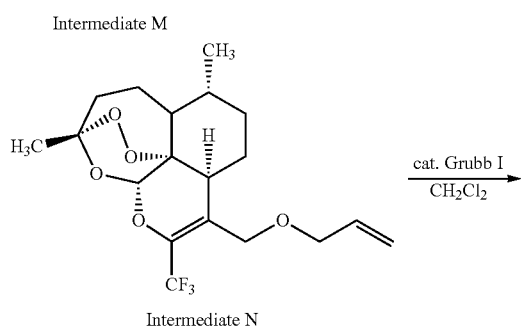

Intermediate N

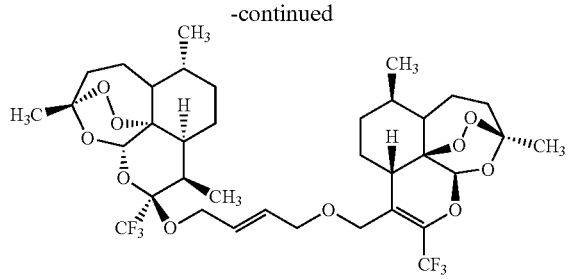

Example 8

1st generation Grubbs' catalyst (cat. Grubb I) (0.031 g, 0.037 mmol, 0.1 eq) is added to a solution of intermediates M (0.147 g, 0.37 mmol, 1 eq) and N (0.146 g, 0.37 mmol, 1 eq) in dichloromethane (3 ml). The mixture is stirred at 40° C. for 20 hours and then cooled and filtered on celite. The solvents are evaporated under reduced pressure. The crude product obtained is purified by silica gel chromatography (95:5 cyclohexane/ethyl acetate); compound 8 is isolated with a yield of 15% (white powder, 0.043 g).

Synthesis of Compound 9

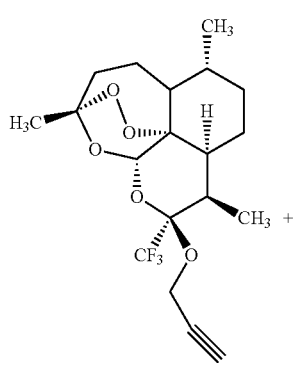

Intermediate L

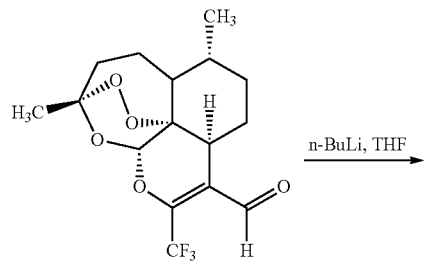

Intermediate C

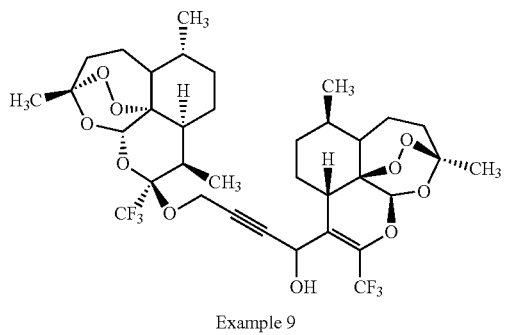

Example 9 n-Butyl-lithium (n-BuLi) (1.6 M in hexane, 100 μl, 0.16 mmol, 1.3 eq) is added drop by drop to a solution of intermediate L (0.047 g, 0.12 mmol) in tetrahydrofuran (1 ml) at −78° C. After 20 minutes of stirring at −78° C., a solution of intermediate C (0.042 g, 0.12 mmol, 1 eq) in tetrahydrofuran (1 ml) is added. The reaction mixture is then returned to room temperature and stirred 16 hours. After adding a saturated ammonium chloride solution, the mixture is extracted with dichloromethane. The organic phase is then dried on magnesium sulphate, filtered and condensed under reduced pressure. The crude product obtained is purified by silica gel chromatography (85:15 cyclohexane/ethyl acetate); compound 9 is isolated with a yield of 40% (white powder, 0.035 g).

Synthesis of Compound 10
Synthesis of Intermediate O:

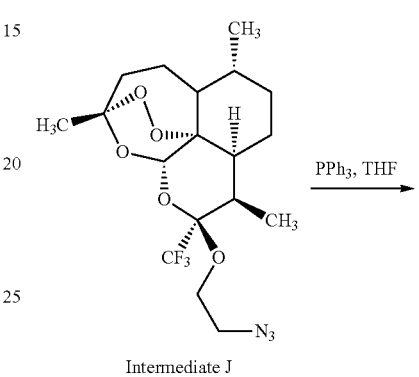

Intermediate J

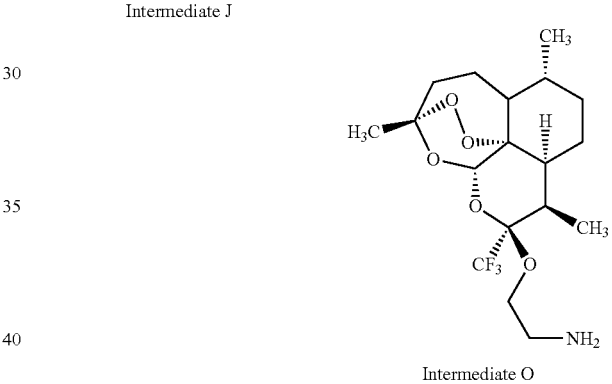

Intermediate O

Triphenylphosphine (PPh$_3$) (0.12 g, 0.45 mmol, 1 eq) is added to a solution of intermediate J (0.19 g, 0.45 mmol) in tetrahydrofuran (4 ml). After 24 hours at room temperature, 2 ml of water is added and stirring is maintained for an additional 24 hours. After evaporation of the solvents under reduced pressure, the crude product obtained is purified by silica gel chromatography (100:0 to 94:6 cyclohexane/ethyl acetate); intermediate O is isolated with a yield of 42% (white powder, 0.075 g).

Coupling of Intermediates A and O:

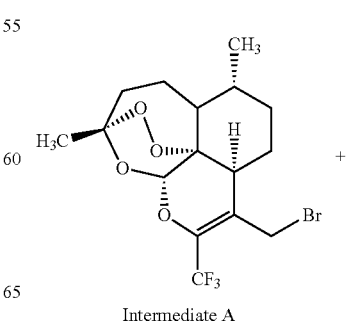

Intermediate A

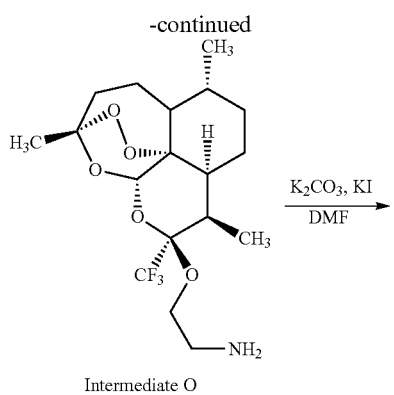

Intermediate O

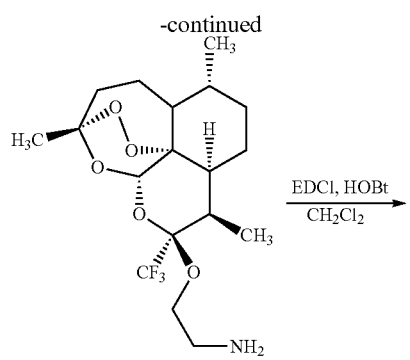

Intermediate O

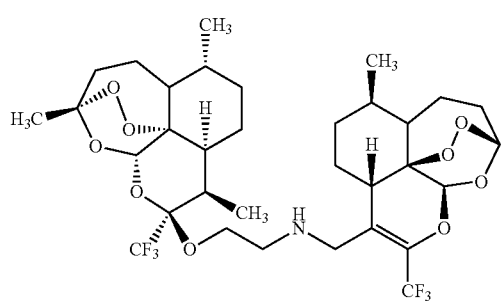

Example 10

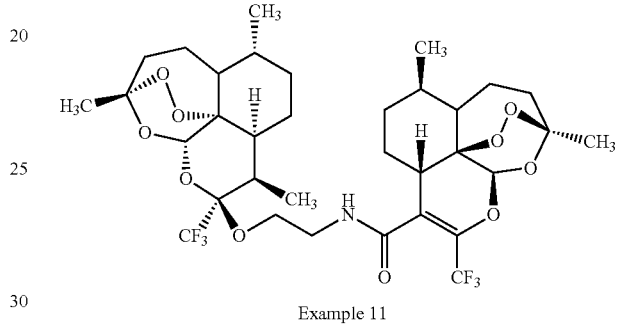

Example 11

Potassium carbonate (0.052 g, 0.37 mmol, 2.2 eq) and potassium iodide (in catalytic quantity) are added to a solution of intermediate A (0.070 g, 0.17 mmol) in dimethylformamide (DMF) (0.5 ml). After 10 minutes of stirring, a solution of intermediate O in dimethylformamide (0.5 ml) is added. The reaction mixture is then heated at 70° C. for 2.5 hours. After returning to room temperature, water and ethyl acetate are added to the medium. The organic phase is washed with saturated sodium chloride solution and dried on magnesium sulphate. After evaporation of the solvents under reduced pressure, the crude product obtained is purified by silica gel chromatography (100:0 to 85:15 dichloromethane/ethyl acetate); compound 10 is isolated with a yield of 34% (pale yellow powder, 0.042 g).

Synthesis of Compound 11

1-(3-Dimethylaminopropyl)-3-ethylcarbodiimide hydrochloride (EDCI) (0.17 g, 0.91 mmol, 3 eq) and 1-hydroxybenzotriazole (HOBt) (0.12 g, 0.91 mmol, 3 eq) are added to a solution of intermediate D (0.11 g, 0.30 mmol) in dichloromethane (5 ml). After 30 minutes of stirring at room temperature, a solution of intermediate O (0.12 g, 0.30 mmol, 1 eq) in dichloromethane (5 ml) is added. The reaction mixture is stirred 2 hours at room temperature. After adding water, the mixture is extracted with dichloromethane. The organic phase is washed with saturated sodium chloride solution and then dried on magnesium sulphate. After filtering, the solvents are evaporated under reduced pressure. The crude product obtained is purified by silica gel chromatography (99:1 to 97:3 dichloromethane/ethyl acetate); compound II is isolated with a yield of 7% (white powder, 0.016 g).

Synthesis of Compounds 12 and 20

Synthesis of Intermediate P:

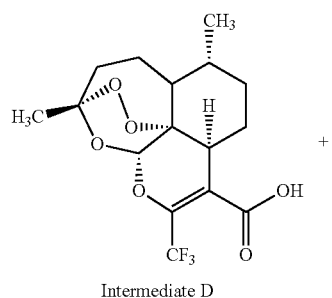

Intermediate D

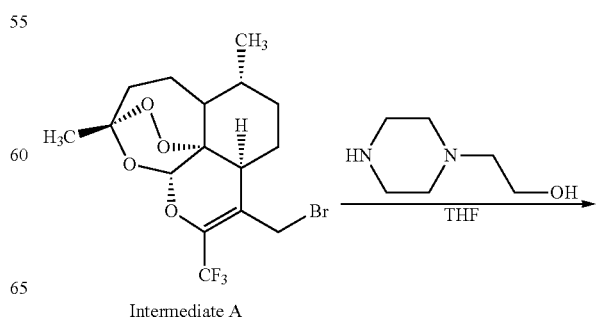

Intermediate A

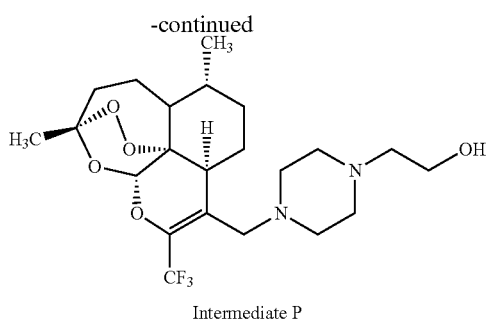

Intermediate P

N-(2-hydroxyethyl)piperazine (1.19 ml, 9.7 mmol, 4 eq) is added to a solution of intermediate A (1 g, 2.4 mmol) in tetrahydrofuran (15 ml) at 0° C. The reaction medium is stirred at 0° C. for 4 hours. After adding water, the mixture is extracted with diethyl ether. The organic phase is washed with saturated sodium chloride solution and then dried on magnesium sulphate. After filtering, the solvents are evaporated under reduced pressure. The crude product obtained is purified by silica gel chromatography (97:3 to 94:6 dichloromethane/methanol); intermediate P is isolated with a yield of 84% (yellow powder, 0.92 g).

Synthesis of Intermediate U:

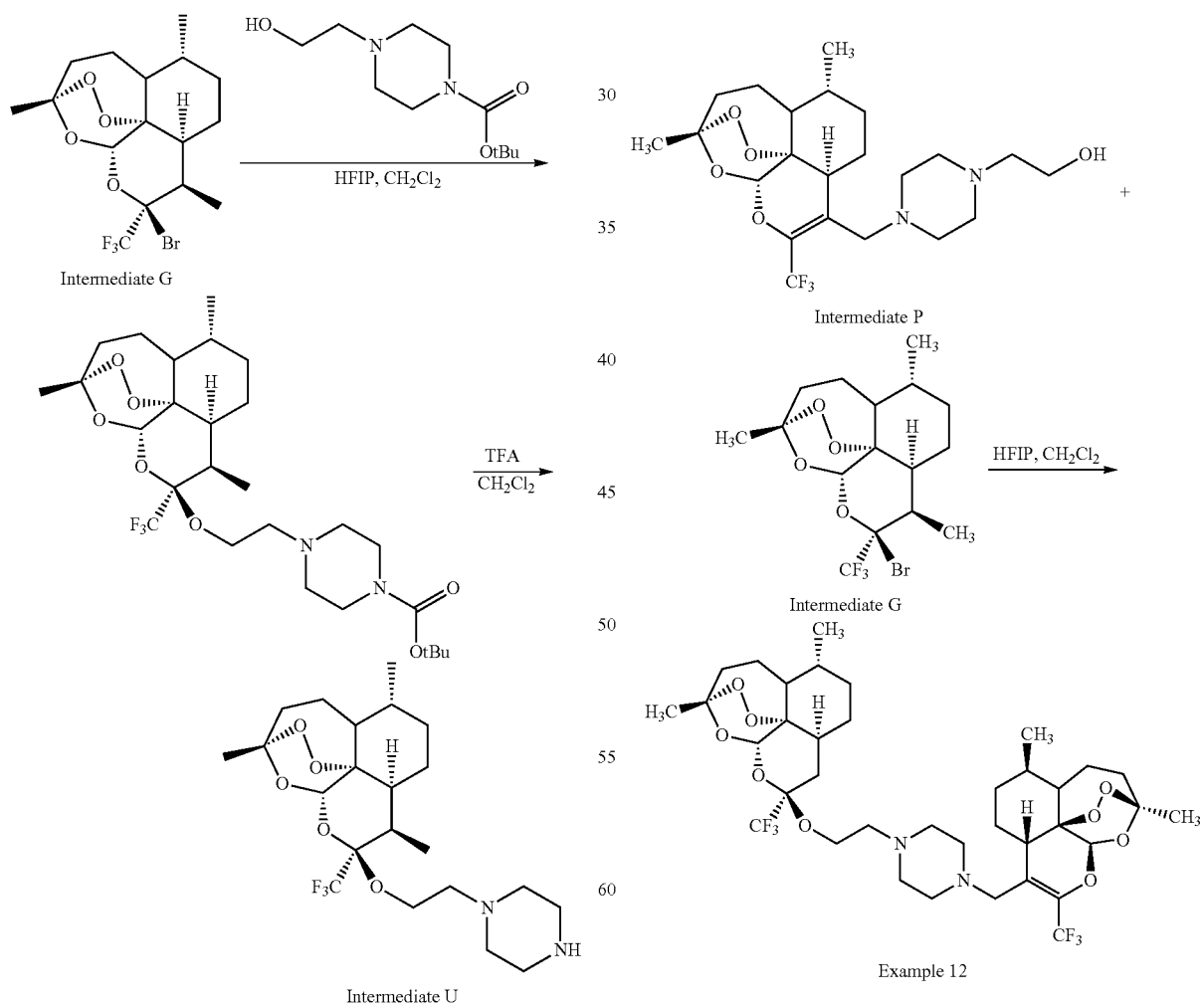

N-Boc-4-(2-hydroxy-ethyl)-piperazine (1.66 g, 7.22 mmol, 5 eq) and hexafluoroisopropanol (HFIP) (0.76 ml, 7.22 mmol, 5 eq) are successively added to a solution of intermediate G (0.60 g, 1.44 mmol) in dichloromethane (6.0 ml). The reaction mixture is stirred at room temperature for 18 hours. The organic phase is washed with sodium hydrogen carbonate solution and then dried on magnesium sulphate. After filtering, the solvents are evaporated under reduced pressure. The crude product obtained is purified by silica gel chromatography (80:20 cyclohexane/ethyl acetate). The expected compound, isolated with a yield of 22% (white powder, 0.18 g), is dissolved in dichloromethane (2.0 ml) to which trifluoroacetic acid (TFA) (0.75 ml) is added. The reaction mixture is stirred for 30 minutes at room temperature and then concentrated under reduced pressure. The residue is diluted in dichloromethane. The organic phase is successively washed with saturated sodium hydrogen carbonate solution and saturated sodium chloride solution, and then dried on sodium sulphate. After filtering, the solvents are evaporated under reduced pressure. The crude product obtained is purified by silica gel chromatography (95:5:0.5 dichloromethane/methanol/aqueous ammonia); intermediate U is isolated with a yield of 61% (white powder, 0.095 g).

Coupling of Intermediates G and P:

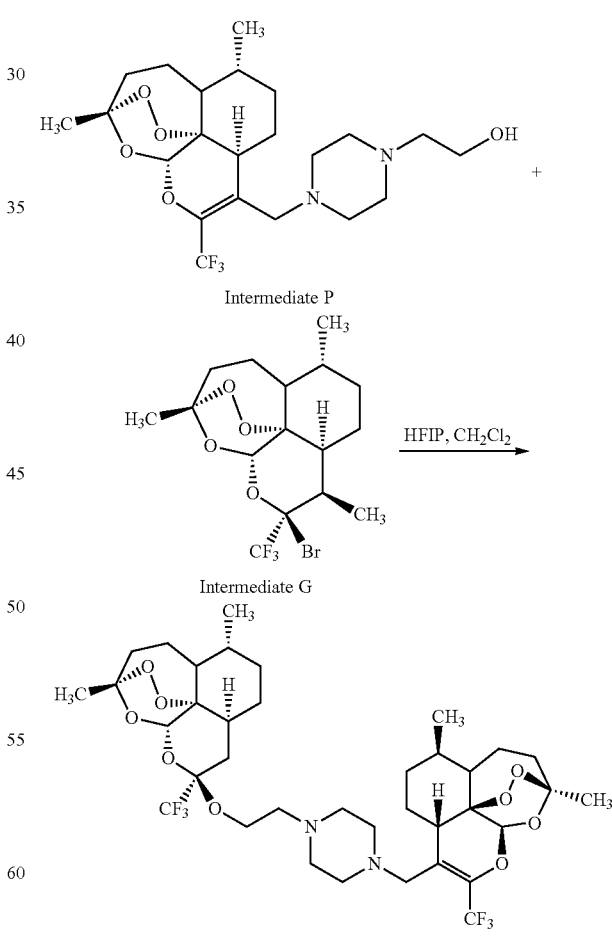

Intermediate P (0.22 g, 0.48 mmol, 2 eq) and hexafluoroisopropanol (127 µl, 1.2 mmol, 5 eq) are successively added to a solution of intermediate G (0.1 g, 0.24 mmol) in dichloromethane (1.5 ml). The reaction mixture is then stirred at room temperature for 2 hours before dilution with dichloromethane. The organic phase is washed with sodium hydrogen carbonate solution and then dried on magnesium sulphate. After filtering, the solvents are evaporated under reduced pressure. The crude product obtained is purified by silica gel chromatography (95:5 to 80:20 cyclohexane/ethyl acetate); compound 12 is isolated with a yield of 6% (pale yellow powder, 0.022 g).

Coupling of Intermediates $A_1$ and U:

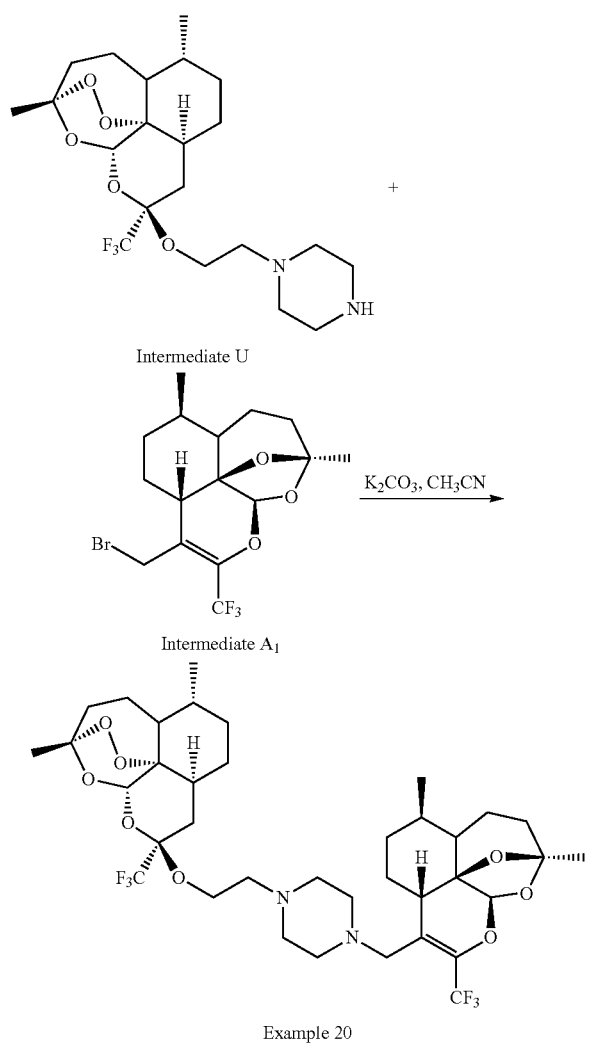

Potassium carbonate (0.21 g, 1.51 mmol, 2 eq) and intermediate $A_1$ (0.30 g, 0.76 mmol, 1 eq) are added to a solution of intermediate U (0.35 g, 0.76 mmol) in acetonitrile (5.0 ml). The reaction mixture is stirred for 2 hours at room temperature before dilution in water and ethyl acetate. The aqueous phase is extracted with ethyl acetate. The combined organic phases are washed with saturated sodium chloride solution and then dried on sodium sulphate. After filtering, the solvents are evaporated under reduced pressure. The crude product obtained is purified by silica gel chromatography (97.5: 2.5 to 92:8 dichloromethane/ethyl acetate); compound 20 is isolated with a yield of 88% (white foam, 0.52 g).

Synthesis of Compound 13

Synthesis of intermediate Q:

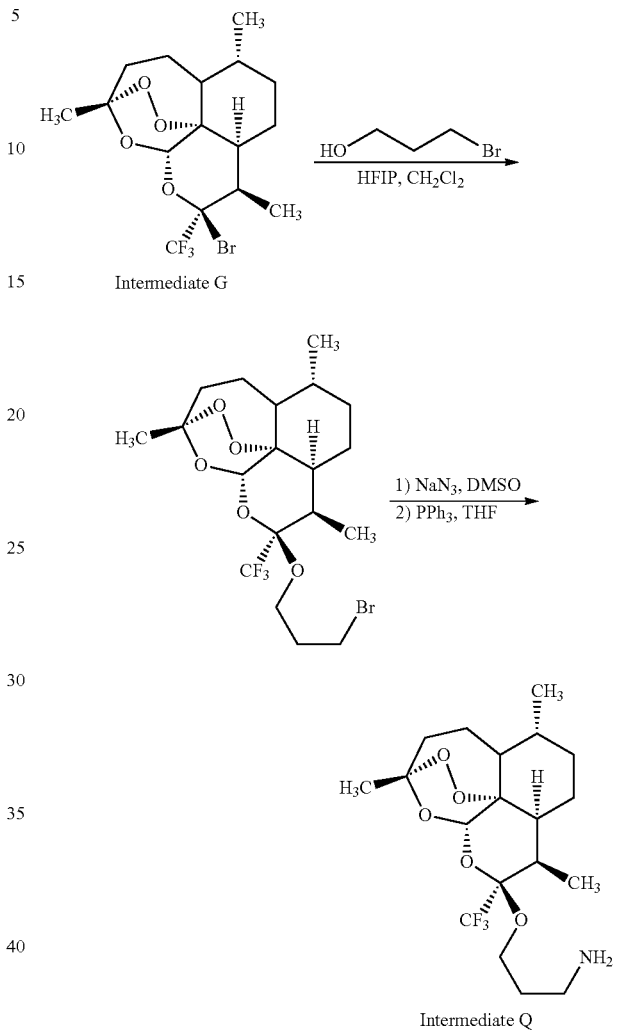

Step 1: 2-Bromo-propanol (2.77 ml, 24.1 mmol, 10 eq) and hexafluoroisopropanol (HFIP) (1.27 ml, 12.0 mmol, 5 eq) are successively added to a solution of intermediate G (1.0 g, 2.41 mmol) in dichloromethane (14 ml). The reaction mixture is then stirred at room temperature for 2.5 hours before dilution with dichloromethane. The organic phase is washed with sodium hydrogen carbonate solution and then dried on magnesium sulphate. After filtering, the solvents are evaporated under reduced pressure. The crude product obtained is purified by silica gel chromatography (95:5 cyclohexane/ethyl acetate); the brominated intermediate is isolated with a yield of 55% (clear oil, 0.63 g).

Step 2: Sodium azide (0.18 g, 2.75 mmol, 2 eq) is added to a solution of the brominated intermediate (0.63 g, 1.38 mmol) in dimethyl sulfoxide (12 ml). The reaction mixture is stirred at room temperature for 2.5 hours. After dilution with ethyl acetate, the organic phase is washed with water and then dried on magnesium sulphate. After filtering, the solvents are evaporated under reduced pressure and the azide intermediate, obtained quantitatively, is used directly in the following step (white powder).

Step 3: Triphenylphosphine (0.36 g, 1.38 mmol, 1 eq) is added to a solution of the azide intermediate (0.60 g, 1.38 mmol) in tetrahydrofuran (6 ml). After 24 hours at room temperature, 2 ml of water is added and stirring is maintained for an additional 24 hours. After evaporation of the solvents under reduced pressure, the crude product obtained is purified by silica gel chromatography (100:0 to 85:15 cyclohexane/ethyl acetate and then 99:1 to 70:30 dichloromethane/methanol); intermediate Q is isolated with a yield of 62% (white powder, 0.35 g).

Coupling of Intermediates D and Q:

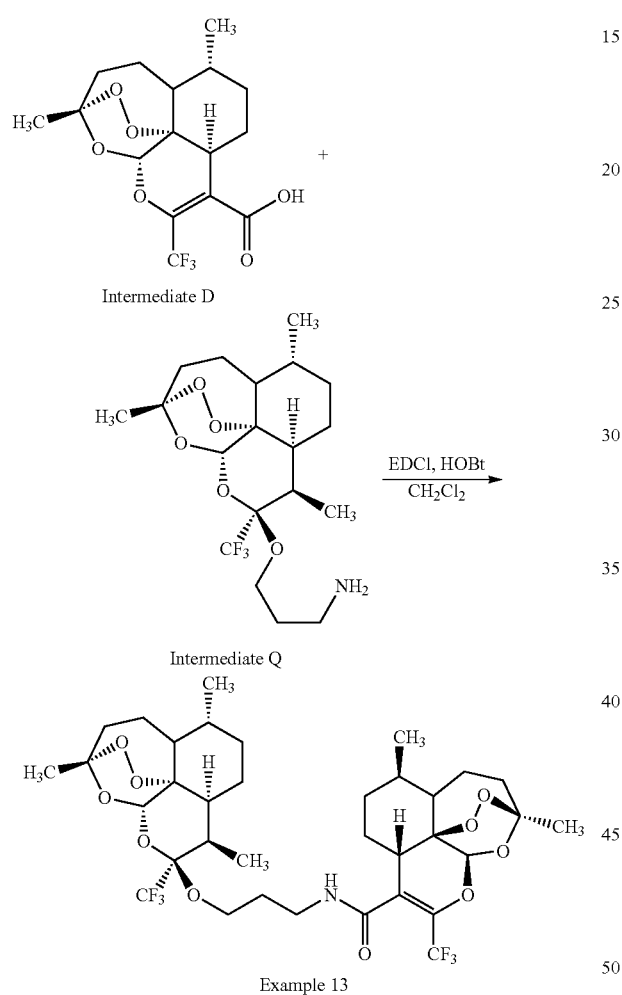

Example 13

EDCI (0.43 g, 2.24 mmol, 3 eq) and HOBt (0.30 g, 2.24 mmol, 3 eq) are added to a solution of intermediate D (0.27 g, 0.74 mmol) in dichloromethane (10 ml). After 30 minutes of stirring at room temperature, a solution of intermediate Q (0.30 g, 0.74 mmol, 1 eq) in dichloromethane (10 ml) is added. The reaction mixture is stirred 2 hours at room temperature. After adding water, the mixture is extracted with dichloromethane. The organic phase is washed with saturated sodium chloride solution and then dried on magnesium sulphate. After filtering, the solvents are evaporated under reduced pressure. The crude product obtained is purified by silica gel chromatography (90:10 to 80:20 cyclohexane/ethyl acetate); compound 13 is isolated with a yield of 59% (white powder, 0.335 g).

Synthesis of Compound 14
Synthesis of Intermediate S:

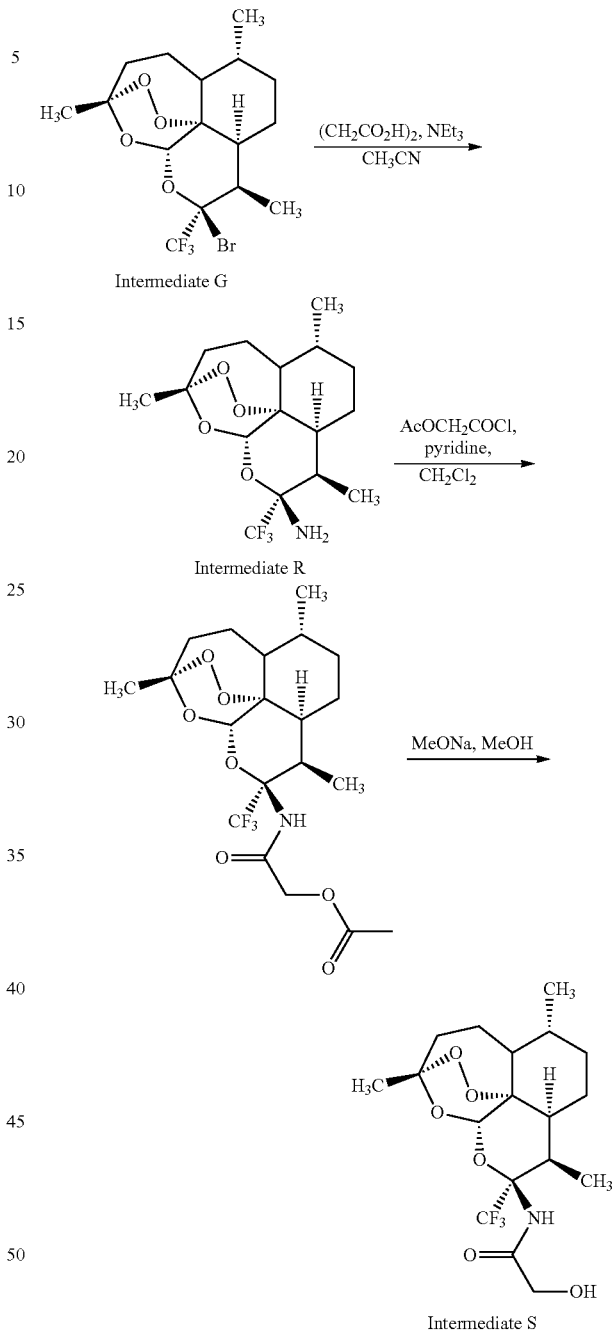

Step 1: Succinic acid (2.84 g, 24.1 mmol, 10 eq) and triethylamine (1.69 ml, 12.0 mmol, 5 eq) are added to a solution of intermediate G (1.0 g, 2.41 mmol) in acetonitrile (10 ml). The reaction mixture is stirred 96 hours at room temperature. Sodium hydrogen carbonate solution is added and the extraction carried out in ethyl acetate. The organic phase is then washed with saturated sodium chloride solution, dried on magnesium sulphate, filtered and then condensed under reduced pressure. The crude product obtained is purified by silica gel chromatography (95:5 to 90:10 cyclohexane/ethyl acetate); intermediate R is isolated with a yield of 33% (beige powder, 0.28 g).

Step 2: Acetoxyacetyl chloride (40 μl, 0.37 mmol, 1.3 eq) and pyridine (30 μl, 0.37 mmol, 1.3 eq) are added to a solution of intermediate R (0.1 g, 0.28 mmol) in dichloromethane (2.5 ml). After 24 hours at room temperature, acyl chloride (1.3 eq) and pyridine (1.3 eq) are again added and the reaction medium is stirred for additional 6 hours. Saturated ammonium chloride solution is added and the mixture extracted with dichloromethane. The organic phase is dried on magnesium sulphate, filtered and then condensed under reduced pressure. The crude product obtained is purified by silica gel chromatography (95:5 to 92.5:7.5 dichloromethane/ethyl acetate); the acetoxy intermediate is isolated with a yield of 44% (white powder, 0.055 g).

Step 3: A sodium methanolate solution (0.010 g, 0.176 mmol) in methanol (0.5 ml) is added to a solution of the acetoxy intermediate (0.053 g, 0.117 mmol) in methanol (2 ml) at 0° C. After 1 hour of stirring at 0° C., the medium is diluted with ethyl acetate and water. The organic phase is then dried on magnesium sulphate, filtered and then condensed under reduced pressure. The crude product obtained is purified by silica gel chromatography (90:10 to 85:15 dichloromethane/ethyl acetate); intermediate S is isolated with a yield of 94% (colorless oil, 0.045 g).

Coupling of Intermediates A and S:

acetonitrile (2 ml). After 5 minutes of stirring, a solution of intermediate A (0.05 g, 0.12 mmol, 1.2 eq) and potassium iodide (in catalytic quantity) in acetonitrile (1 ml) is added. The reaction mixture is stirred at room temperature for 30 hours (with additional sodium hydride (2.5 eq) added). After adding saturated sodium hydrogen carbonate solution, extraction is carried out in ethyl acetate. The organic phase is then dried on magnesium sulphate, filtered and condensed under reduced pressure. The crude product obtained is purified by silica gel chromatography (85:15 to 75:25 cyclohexane/ethyl acetate); compound 14 is isolated with a yield of 21% (white powder, 0.016 g).

Synthesis of Compound 15

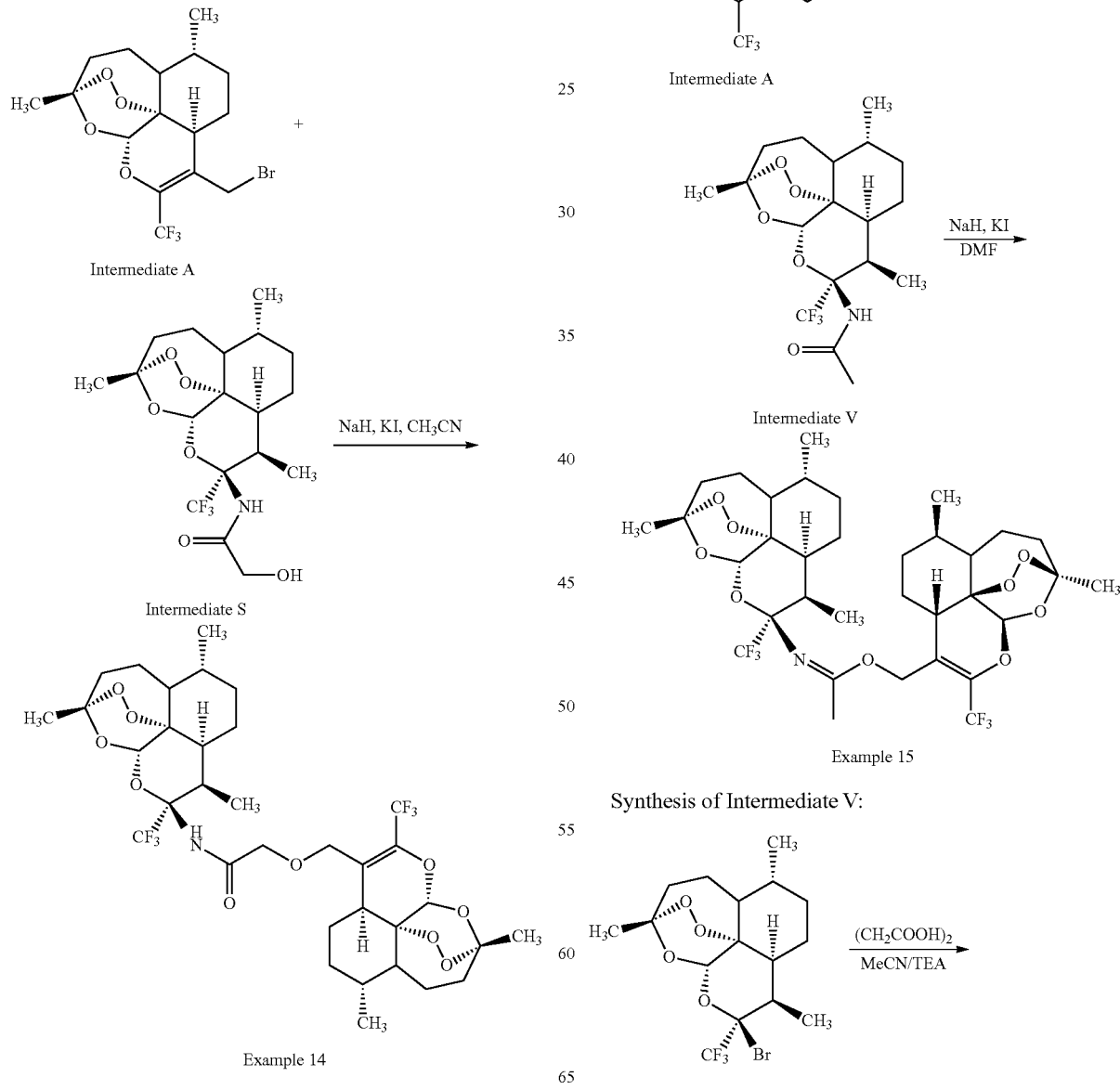

Sodium hydride (60% in oil, 0.01 g, 0.25 mmol, 2.5 eq) is added to a solution of intermediate S (0.04 g, 0.1 mmol) in

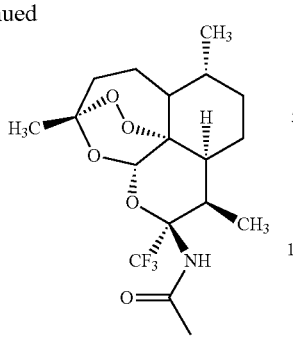

Intermediate V

Succinic acid (4.19 g, 35.5 mmol, 10 eq) and triethylamine (1.80 g, 17.7 mmol, 5 eq) are successively added at room temperature to a solution of intermediate G (1.47 g, 3.5 mmol, 1 eq) in acetonitrile. After 3 days of stirring at room temperature, the reaction medium is diluted with ethyl acetate (60 ml) and is washed with saturated NaHCO$_3$ solution (30 ml). The organic phase is dried on MgSO$_4$, filtered and then concentrated under reduced pressure. The crude reaction product is purified by silica gel column chromatography with an eluent gradient (100:0 to 40:60 cyclohexane/ethyl acetate). Intermediate V is obtained with a yield of 30% (401 mg).

Coupling of Intermediates A and V:

Sodium hydride (60% in oil, 0.02 g, 0.51 mmol, 2 eq) is added to a solution of intermediate V (0.1 g, 0.25 mmol) in dimethylformamide (1.2 ml) at 0° C. After 5 minutes of stirring, intermediate A (0.21 g, 0.51 mmol, 2 eq) and potassium iodide (0.01 g, 0.05 mmol, 0.2 eq) are added. The reaction mixture is stirred at room temperature for 2 hours. After hydrolysis with saturated sodium chloride solution, the reaction mixture is extracted with diethyl ether and then the organic phase is dried on magnesium sulphate, filtered and condensed under reduced pressure. The crude product obtained is purified by silica gel chromatography (98:2 to 90:10 petroleum ether/diethyl ether); compound 15 is isolated with a yield of 40% (white powder, 0.073 g).

Synthesis of Compound 21

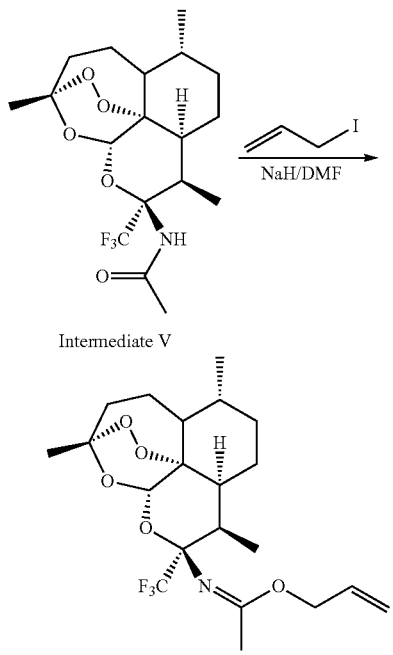

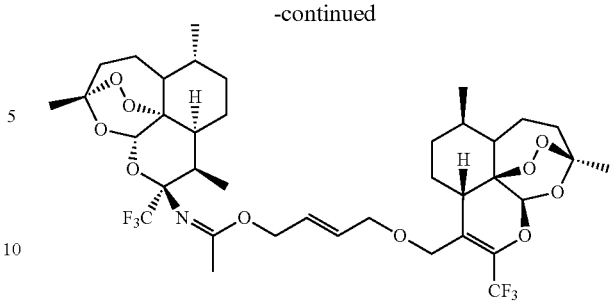

Example 21

Step 1: Sodium hydride (76 mg, 1.9 mmol, 3 eq) and then allyl iodide (174 µl, 1.9 mmol, 3 eq) are added at 0° C. to a solution of intermediate V (250 mg, 0.635 mmol) in anhydrous dimethylformamide (DMF) (4 ml). The reaction medium is allowed to return to room temperature. After 4.5 hours of stirring, it is hydrolyzed with saturated NaCl solution. The organic phase is dried on MgSO$_4$, filtered and then evaporated under reduced pressure. The O-allyl imino ether (277 mg, 80%) is obtained after purification by silica gel chromatography with an eluent gradient (98:2 to 95:5 petroleum ether/diethyl ether).

Step 2: The O-allyl imino ether (174 mg, 0.401 mmol, 1 eq) isolated above and then 1$^{st}$ generation Grubbs' catalyst (33 mg, 0.043 mmol, 0.1 eq) are added to a solution of intermediate N (131 mg, 0.335 mmol, 0.8 eq) in dichloromethane (1.6 ml). After 23 hours of stirring at room temperature, the reaction medium is filtered on silica and then concentrated under reduced pressure. Compound 21 (47 mg, 15%) is obtained after purification by silica gel chromatography with an eluent gradient (100:0 to 85:15 cyclohexane/ethyl acetate).

Synthesis of Compounds 22, 23 and 24

Synthesis of Intermediate Wa:

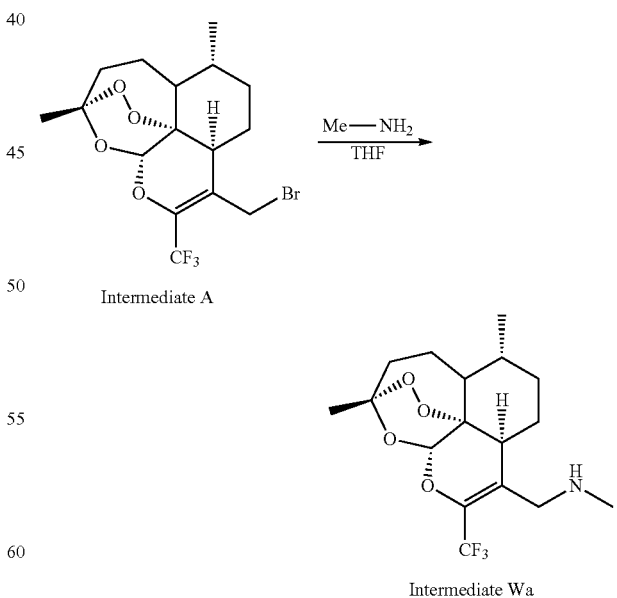

A solution of intermediate A (100 mg, 0.241 mmol) in anhydrous THF (1.2 ml) is added over 45 minutes, at 0° C. and under argon, to a solution of methylamine [8.03 M in ethanol (300 µl, 2.41 mmol, 10 eq)] in anhydrous tetrahydrofuran (THF) (12.5 ml). After 2 hours of stirring at room temperature, the reaction is diluted in diethyl ether and is washed with saturated NaCl solution. The organic phase is dried on $MgSO_4$, filtered and concentrated under reduced pressure. The crude reaction product is purified by silica gel chromatography with an eluent gradient (80:20 to 10:90 cyclohexane/ethyl acetate). Intermediate Wa is obtained with a yield of 85% (75 mg).

Synthesis of Intermediate Wb:

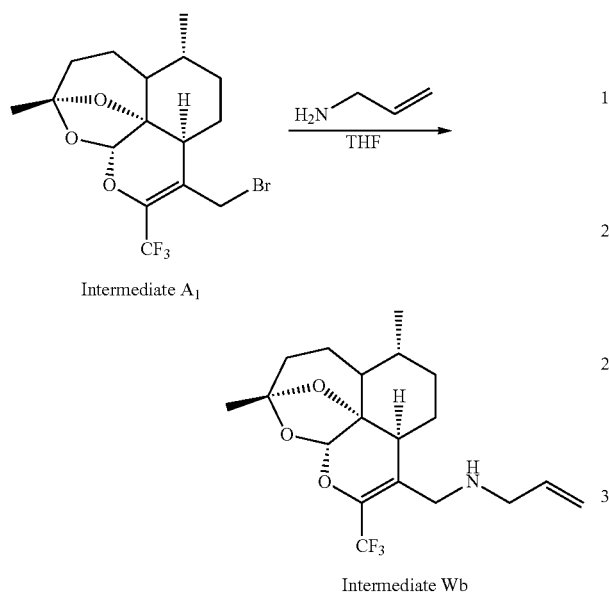

Intermediate Wb is obtained according to the same method with a yield of 47% by reaction of intermediate $A_1$ with allylamine.

Synthesis of Intermediate Xa:

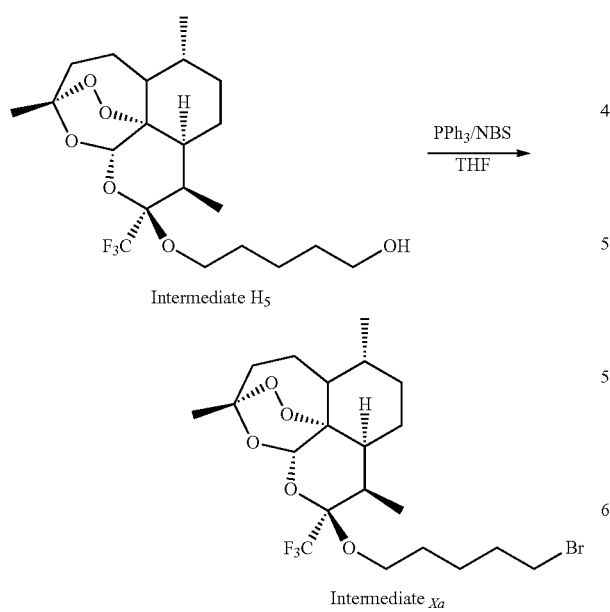

Triphenylphosphine (78 mg, 0.301 mmol, 1.2 eq) and then N-bromosuccinimide (NBS) (67 mg, 0.376 mmol, 1.5 eq) are added to a solution of intermediate $H_5$ (110 mg, 0.250 mmol) in anhydrous THF (1 ml) at −15° C. and under argon. The reaction medium is allowed to rise to room temperature. After 1 hour of additional stirring, the reaction is diluted in diethyl ether and is washed with saturated NaCl solution. The organic phase is dried on $MgSO_4$, filtered and concentrated under reduced pressure. The crude reaction product is purified by silica gel chromatography with an eluent gradient (100:0 to 95:5 cyclohexane/ethyl acetate). Intermediate Xa is obtained with a yield of 75% (92 mg).

Synthesis of Intermediate Xb:

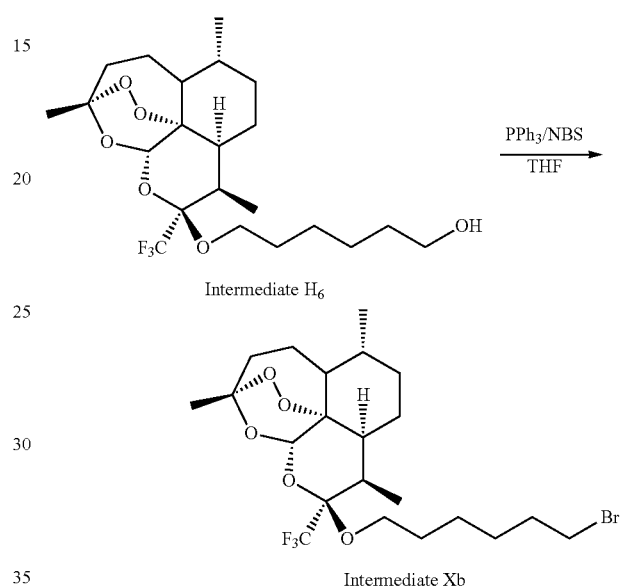

Intermediate Xb is obtained according to the same method with a yield of 89% from intermediate $H_6$.

Synthesis of Intermediate Xc:

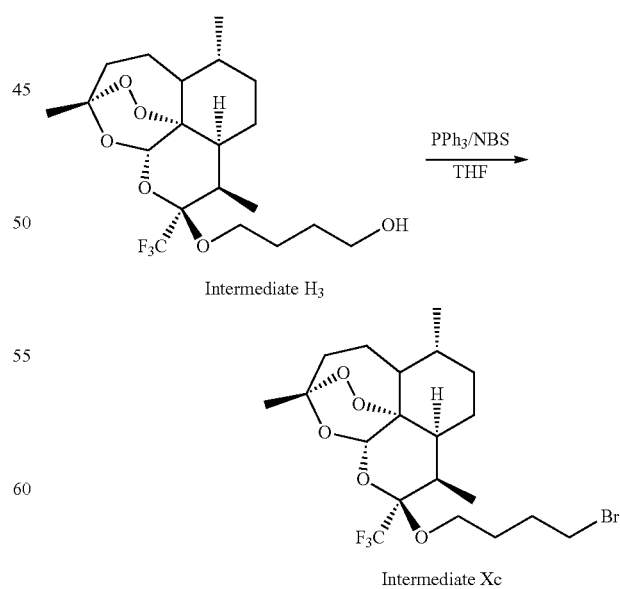

Intermediate Xc is obtained according to the same method with a yield of 86% from intermediate $H_3$.

Coupling of Intermediates W and X:

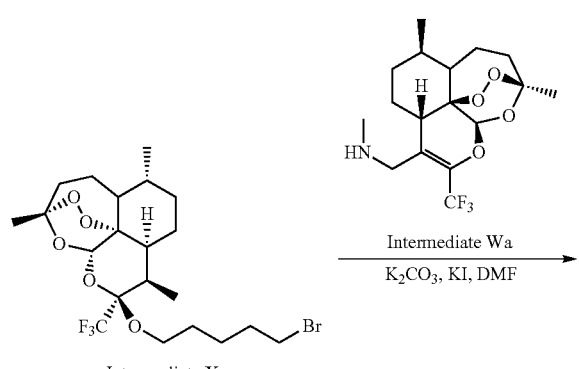

Intermediate Xa

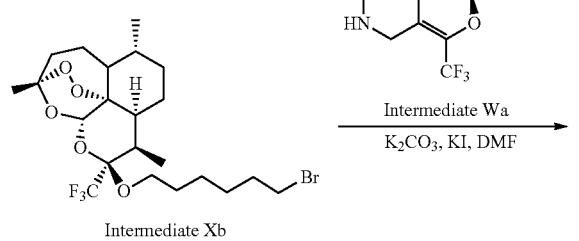

Example 22

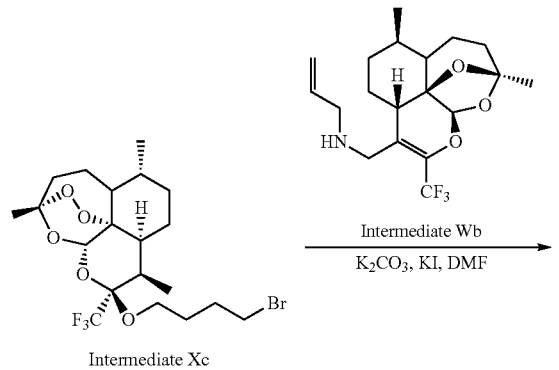

Intermediate Xb

Example 23

Intermediate Xc

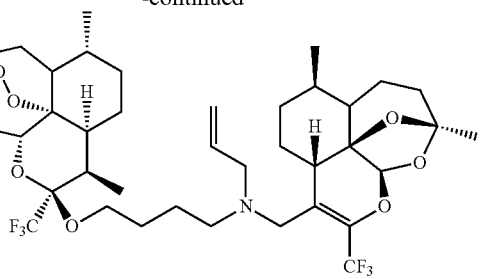

Example 24

Potassium iodide (34 mg, 0.204 mmol, 1.1 eq), potassium carbonate (57 mg, 0.411 mmol, 2.2 eq) and then intermediate Wa (74 mg, 0.203 mmol, 1.0 eq) in solution in anhydrous DMF (1.0 ml) are added, at room temperature and under argon, to a solution of intermediate Xa (93 mg, 0.186 mmol) in anhydrous DMF (1.6 ml). The reaction medium is heated at 75° C. for 1.5 hours. Once cooled, the reaction mixture is diluted with dichloromethane (5 ml), washed with saturated $NaHCO_3$ solution (5 ml) and then with saturated NaCl solution (5 ml). The organic phase is dried on $MgSO_4$, filtered and then evaporated under reduced pressure. The crude reaction product is purified by silica gel chromatography with an eluent gradient (100:0 to 92:8 cyclohexane/ethyl acetate). Compound 22 is obtained with a yield of 70% (105 mg).

Compound 23 is obtained with a yield of 18% following the same procedure, by coupling intermediate Wa with intermediate Xb.

Compound 24 is obtained with a yield of 76% following the same procedure, by coupling intermediate Wb with intermediate Xc.

Synthesis of Compound 25

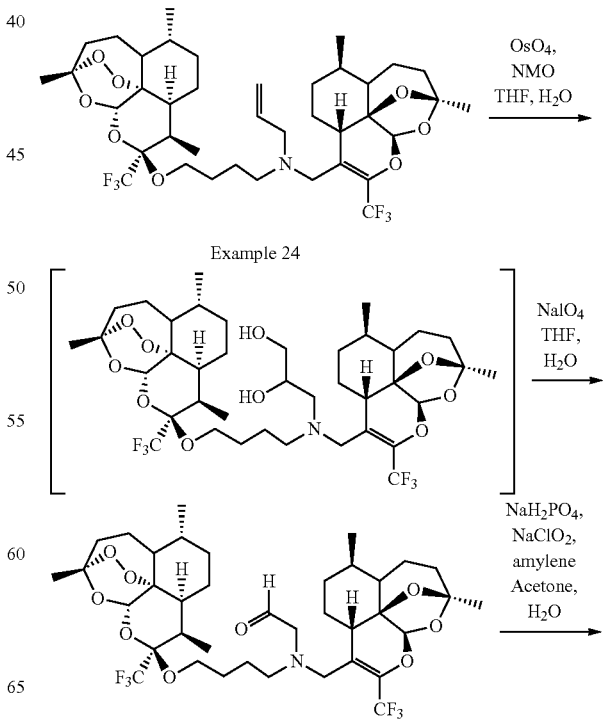

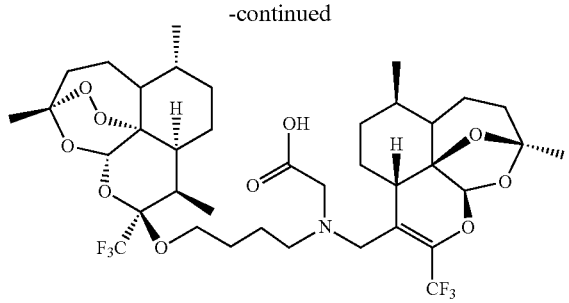

Example 25

Step 1: OsO₄ (0.98 ml, 0.15 mmol, 0.3 eq) and N-methylmorpholine oxide (NMO) (78.1 mg, 0.67 mmol, 1.3 eq) are added to a solution of compound 24 (0.4 g, 0.51 mmol) in tetrahydrofuran (20.0 ml) and water (5.0 ml). The reaction mixture is stirred at room temperature for 18 hours. Water (15.0 ml) and NaIO₄ (0.55 g, 2.56 mmol, 10 eq) are added, and the reaction mixture is stirred for 1 hour at room temperature, before being diluted by adding water and ethyl acetate. The organic phase is washed with saturated sodium thiosulphate solution and saturated sodium chloride solution, and then is dried on magnesium sulphate. After filtering, the solvents are evaporated under reduced pressure.

Step 2: Sodium phosphate (0.23 g, 1.70 mmol, 3 eq), amylene (0.27 ml, 2.55 mmol, 4.5 eq) and sodium chlorite (0.15 g, 1.70 mmol, 3 eq) are added to a solution of the crude aldehyde previously formed (0.44 g, 0.57 mmol) in acetone (15.0 ml) and water (8.0 ml). The reaction mixture is stirred at room temperature for 18 hours before being diluted in water and ethyl acetate. The aqueous phase is extracted with ethyl acetate. The combined organic phases are washed with water and with saturated sodium chloride solution, and then dried on magnesium sulphate. After filtering, the solvents are evaporated under reduced pressure. The crude reaction product is purified by silica gel chromatography (50:50 ethyl acetate/methanol). Compound 25 is obtained with a yield of 18% (beige gum, 0.082 g).

Synthesis of Compound 26

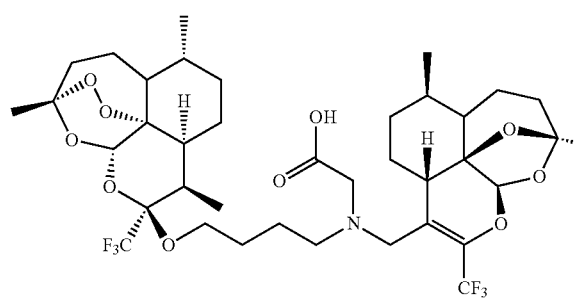

Example 25

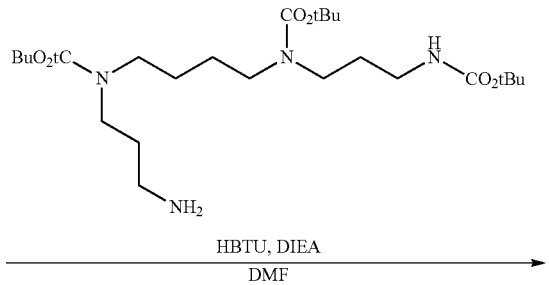

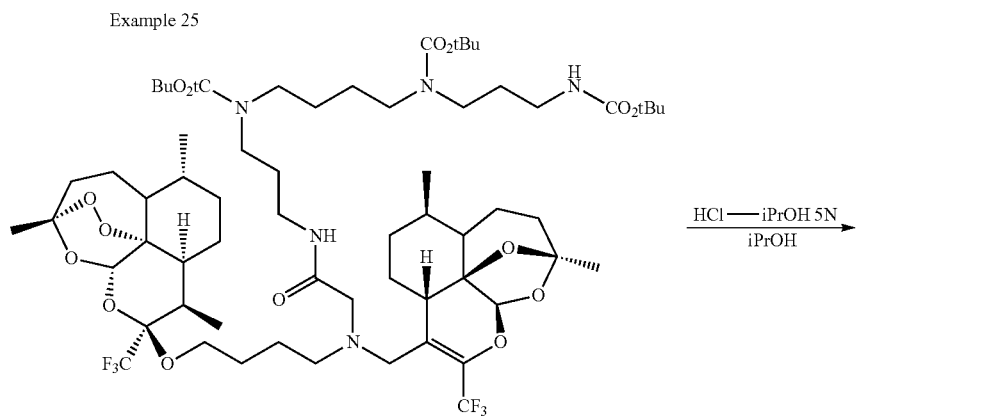

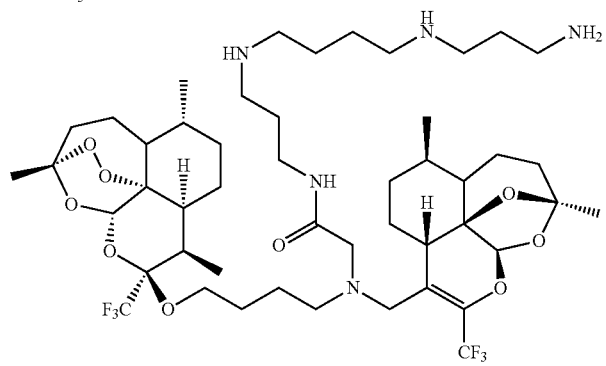

Example 26

Step 1: Polyamine (0.045 g, 0.089 mmol, 1 eq), 2-(1H-benzotriazole-1-yl)-1,1,3,3-tetramethyluronium hexafluorophosphate (HBTU) (0.044 g, 0.12 mmol, 1.3 eq) and diisopropylethylamine (DIEA) (0.04 ml, 0.22 mmol, 2.5 eq) are added to a solution of 26 (0.07 g, 0.089 mmol) in N,N-dimethylformamide (1.0 ml). The reaction mixture is stirred for 6 hours at room temperature before being diluted in water and ethyl acetate. The aqueous phase is extracted with ethyl acetate. The combined organic phases are washed with water and with saturated sodium chloride solution, and then dried on magnesium sulphate. After filtering, the solvents are evaporated under reduced pressure. The crude reaction product is purified by silica gel chromatography (90:10 to 70:30 dichloromethane/ethyl acetate); the expected product is obtained with a yield of 44% (0.050 g).

Step 2: A 5 N hydrochloric acid solution in isopropyl alcohol (1.0 ml) is added to a solution of the intermediate obtained previously (0.05 g, 0.039 mmol) in isopropyl alcohol (3.0 ml). The reaction mixture is stirred at room temperature for 18 hours and then is concentrated under reduced pressure. Compound 26 is obtained with a yield of 39% in the form of hydrochloride (white solid, 0.015 g).

Synthesis of Compounds 27 and 28

OsO$_4$ (0.36 ml, 0.042 mmol, 0.3 eq) and NMO (25 mg, 0.2 mmol, 1.5 eq) are added to a solution of compound 8 (0.11 g, 0.14 mmol) in tetrahydrofuran (3.5 ml) and water (0.9 ml). The reaction mixture is stirred at room temperature for 18 hours. The organic phase is washed with saturated sodium thiosulphate solution, saturated sodium chloride solution, and then is dried on magnesium sulphate. After filtering, the solvents are evaporated under reduced pressure. The crude mixture is purified by silica gel chromatography (100:0 to 70:30 cyclohexane/ethyl acetate). Compound 27 is obtained with a yield of 36% (beige foam, 0.041 g). Compound 28 is obtained with a yield of 13% (beige foam, 0.015 g).

Synthesis of Compound 29
Synthesis of Intermediate Y

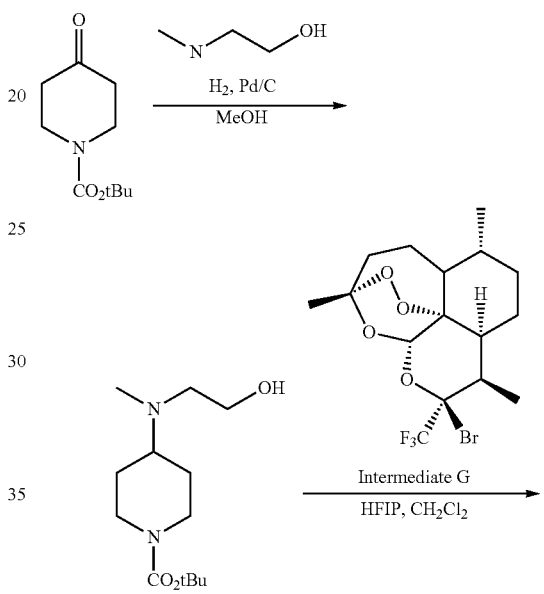

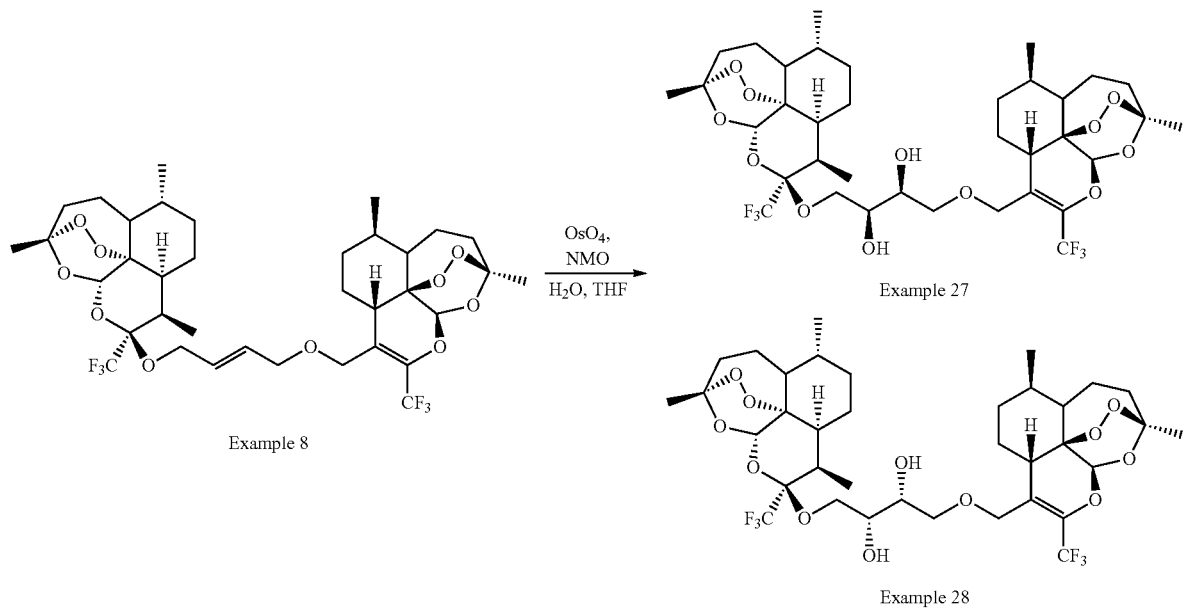

-continued

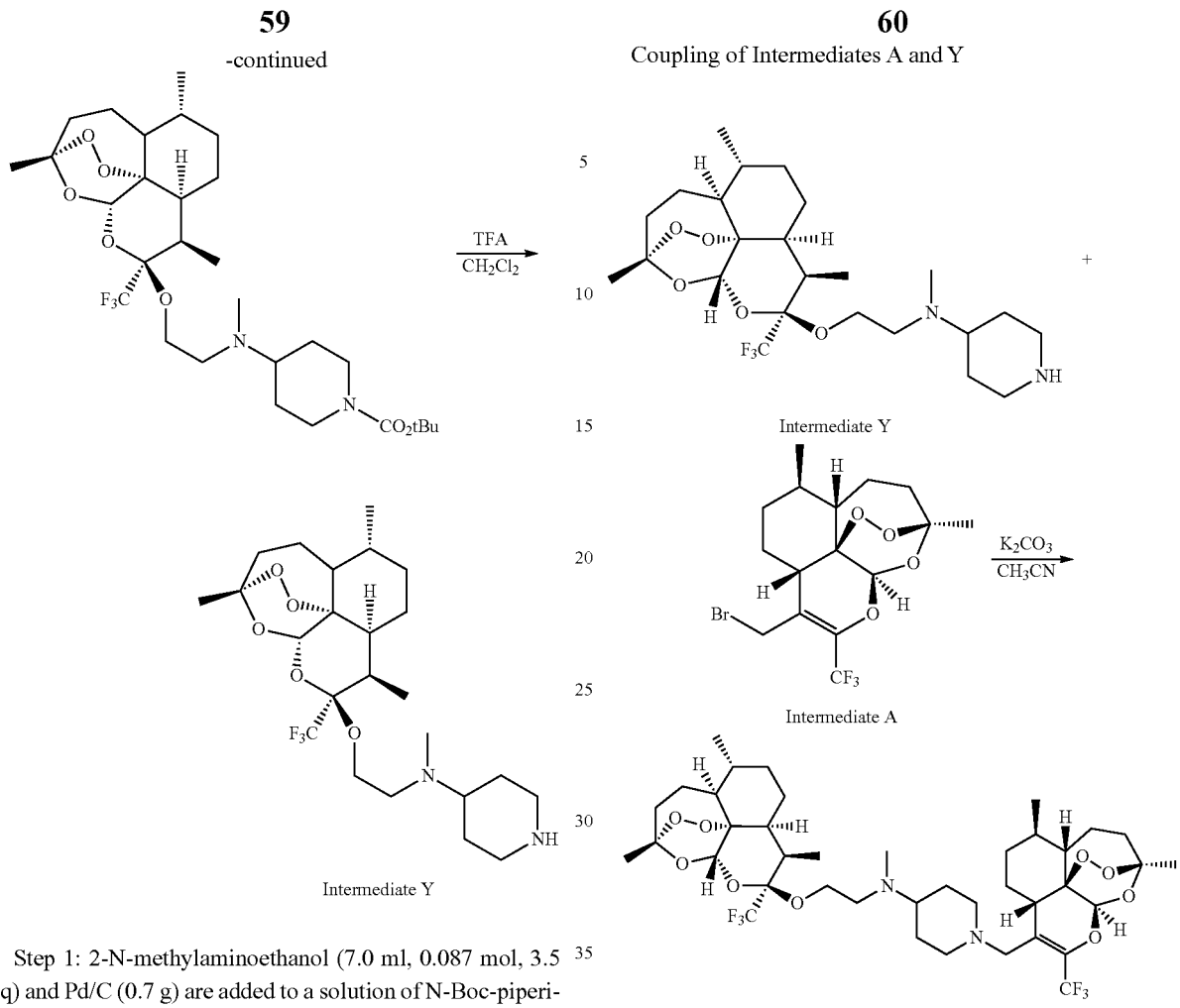

Step 1: 2-N-methylaminoethanol (7.0 ml, 0.087 mol, 3.5 eq) and Pd/C (0.7 g) are added to a solution of N-Boc-piperidone (5.0 g, 0.025 mol) in methanol (85 ml). The reaction mixture is stirred at room temperature under atmosphere of hydrogen for 18 hours. The mixture is then filtered on celite, and the solvents are evaporated under reduced pressure. The crude product is then purified by silica gel chromatography (85:15 dichloromethane/methanol). The expected intermediate is obtained with a yield of 97% (yellow oil, 6.4 g).

Step 2: A solution of intermediate G (1.0 g, 2.42 mmol), the intermediate previously formed (6.4 g, 25.6 mmol) and hexafluoroisopropanol (HFIP) (1.9 ml, 18.1 mmol) is stirred at room temperature for 14 days. The solvents are then evaporated under reduced pressure, and the crude reaction product is purified by silica gel chromatography (100:0 to 97:3 dichloromethane/methanol). The expected intermediate is obtained with a yield of 15% (0.21 g).

Step 3: Trifluoroacetic acid (TFA) (0.6 ml) is added to a solution of the intermediate previously formed (0.21 g, 0.36 mmol) in dichloromethane (2.0 ml). The reaction mixture is stirred at room temperature for 3 hours, and then basified by adding potassium carbonate aqueous solution. The aqueous phase is extracted with dichloromethane. The combined organic phases are dried on magnesium sulphate. After filtering, the solvent is evaporated under reduced pressure. The crude is purified by silica gel chromatography (80:20:1 to 70:30:1 dichloromethane/methanol/aqueous ammonia); intermediate Y is obtained with a yield of 42% (yellow oil, 0.074 g).

Coupling of Intermediates A and Y

Potassium carbonate (0.023 g, 0.16 mmol, 1.1 eq) and intermediate A (0.068 g, 0.16 mmol, 1.1 eq) are added to a solution of intermediate Y (0.074 g, 0.15 mmol) in acetonitrile (1.0 ml). The reaction mixture is stirred and heated at 90° C. for 18 hours. The mixture is then cooled to room temperature and diluted in water and ethyl acetate. The aqueous phase is extracted with ethyl acetate. The combined organic phases are washed with water and with saturated sodium chloride solution, and then dried on magnesium sulphate. After filtering, the solvents are evaporated under reduced pressure. The crude reaction product is purified by silica gel chromatography (60:40 to 40:60 cyclohexane/ethyl acetate); compound 29 is obtained with a yield of 7% (white solid, 0.008 g).

Example 2

Cytotoxic Activity of the Compounds of the Invention

The cytotoxic activity of the compounds of the invention was evaluated by measuring inhibition of cell proliferation of human tumour cell lines, such as the A549 cell line (lung) and the Namalwa cell line (lymphoma). This activity is expressed by $IC_{50}$, the concentration of the product tested able to inhibit cell proliferation by 50%. The method employed is measurement by luminescence of residual ATP after 72 hours of incubation using the ATPLite® kit sold by Perkin Elmer, as described in the following publication: "Measurement of cytotoxicity by ATP-based luminescence assay in primary cell cultures and cell lines." I. A. Cree, P. E. Andreotti, *Toxicology in Vitro*, 11, 553-6, (1997).

As an example, the cytotoxic properties of a few of the compounds of the invention evaluated on A549 and Namalwa cell lines are presented in the following table:

| | $IC_{50}$ (expressed in nM) | |
|---|---|---|
| Product | A549 | Namalwa |
| 1 | 5.2 | 6.8 |
| 2 | 25 | 27 |
| 3 | 6.7 | 5.5 |
| 4 | 27 | 19 |
| 7 | 45 | 30 |
| 8 | 27 | 13 |
| 10 | 27 | 19 |
| 16 | 19 | 42 |
| 17 | 62 | 130 |
| 21 | 30 | 35 |
| 22 | 46 | 83 |
| 28 | 22 | 21 |

Taking into account these cytotoxic properties, the compounds of the invention can be used in human therapeutics to treat cancer pathology. Pharmaceutical preparations containing these active ingredients can be formulated for administration notably by oral, intravenous or subcutaneous route.

The invention claimed is:
1. A dimeric derivative of 10-trifluoromethylated artemisinin of formula (I):

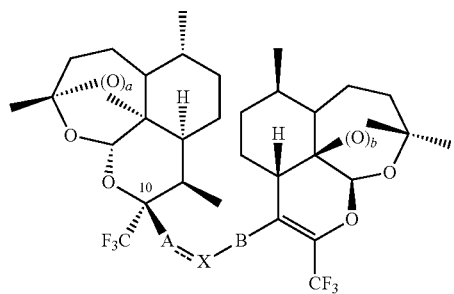

or a pharmaceutically acceptable salt thereof,
wherein:
a and b represent 2,
A represents:
a heteroatom selected from an atom of nitrogen, oxygen and sulphur, the nitrogen atom being optionally substituted by a radical R1 selected from a hydrogen atom and the following groups: $(C_1\text{-}C_6)$alkyl, $(C_2\text{-}C_6)$alkenyl, $(C_2\text{-}C_6)$alkynyl, $(C_3\text{-}C_8)$cycloalkyl, aryl-$(C_1\text{-}C_6)$alkyl, heteroaryl-$(C_1\text{-}C_6)$alkyl, heterocycle-$(C_1\text{-}C_6)$alkyl, optionally substituted aryl, optionally substituted heteroaryl, —COR2, —$CO_2$R2, —C(O)NR2R2a, —$SO_2$R2, —$CH_2$C(O)OR2 and —$CH_2$C(O)NR2R2a, with R2 representing a hydrogen atom or one of the following groups: $(C_1\text{-}C_6)$alkyl, $(C_2\text{-}C_6)$alkenyl, $(C_2\text{-}C_6)$alkynyl, optionally substituted polyamine, $(C_3\text{-}C_8)$cycloalkyl, aryl-$(C_1\text{-}C_6)$alkyl, heteroaryl-$(C_1\text{-}C_6)$alkyl, optionally substituted aryl or optionally substituted heteroaryl, and R2a representing a hydrogen atom or a $(C_1\text{-}C_6)$alkyl group, or a saturated heterocycle comprising one or more heteroatoms selected from atoms of oxygen, sulphur and nitrogen, of which at least one nitrogen atom is linked to carbon 10,

- - - - represents a single bond when A represents an atom of oxygen or sulphur or a heterocycle, or represents a single bond or a double bond when A represents a nitrogen atom, the aforesaid nitrogen atom being substituted by a radical R1 as defined above when - - - - represents a single bond, B represents a —$CH_2$—Y—, —C(=O)—Y— or —CH(OR3)-group, with Y representing O, S, N—R1 or a heterocycle, with R1 as defined above, and R3 representing a hydrogen atom or a $(C_1\text{-}C_6)$alkyl or aryl group, and X represents:
when - - - - represents a double bond:
a =C(X1)-(O—X2)$_c$-group with X1 and X2 representing, independently of each other, a $(C_1\text{-}C_6)$alkyl or $(C_2\text{-}C_6)$alkenyl group and c representing 0 or 1, or when - - - - represents a single bond:
one of the following groups: $(C_1\text{-}C_6)$alkyl optionally substituted by one or more OH groups; $(C_2\text{-}C_6)$alkenyl; $(C_2\text{-}C_6)$alkynyl; $[(C_1\text{-}C_6)$alkyl$]_n$-$(C_3\text{-}C_8)$cycloalkyl-$[(C_1\text{-}C_6)$alkyl$]_p$; $[(C_1\text{-}C_6)$alkyl$]_n$-heterocycle$[(C_1\text{-}C_6)$alkyl$]_p$; $[(C_1\text{-}C_6)$alkyl$]_n$-aryl-$[(C_1\text{-}C_6)$alkyl$]_p$; $[(C_1\text{-}C_6)$alkyl$]_n$-heteroaryl-$[(C_1\text{-}C_6)$alkyl$]_p$; with n and p representing, independently of each other, 0 or 1, a —CO—$(CH_2)_q$— or —CO—$(CH_2)_q$—CO— group for which q represents an integer equal to 1, 2, 3 or 4, or a —CO$_r$—$(CH_2)_s$—Z—$(CH_2)_t$—CO$_u$— group for which r and u represent, independently of each other, an integer equal to 0 or 1, s and t represent, independently of each other, an integer equal to 0, 1, 2, 3 or 4, and Z represents an —S—, —S—S—, —SO—, —$SO_2$—, —Se—Se—, —O—P(O)(OR3)-O—, —NR1-, $(C_3\text{-}C_8)$-cycloalkyl, aryl or heteroaryl group, with R1 and R3 as defined above.

2. The dimeric derivative of claim 1, wherein A represents an oxygen or nitrogen atom.

3. The dimeric derivative of claim 1, wherein B represents a —$CH_2$O—, —$CH_2$NR1-, —C(=O)NR1-, —CH(OR3)- or —$CH_2$-(heterocycle)-group, with R1 and R3 as defined in claim 1.

4. The dimeric derivative of claim 1, wherein - - - - represents a single bond and X represents a $(C_1\text{-}C_6)$alkyl, $(C_2\text{-}C_6)$alkenyl, $(C_2\text{-}C_6)$alkynyl, $(C_1\text{-}C_6)$alkyl-heteroaryl-$(C_1\text{-}C_6)$alkyl, —$(CH_2)_q$—NR1- or —CO—$(CH_2)_q$— group, with q as defined in claim 1.

5. The dimeric derivative of claim 1 selected from the following compounds:

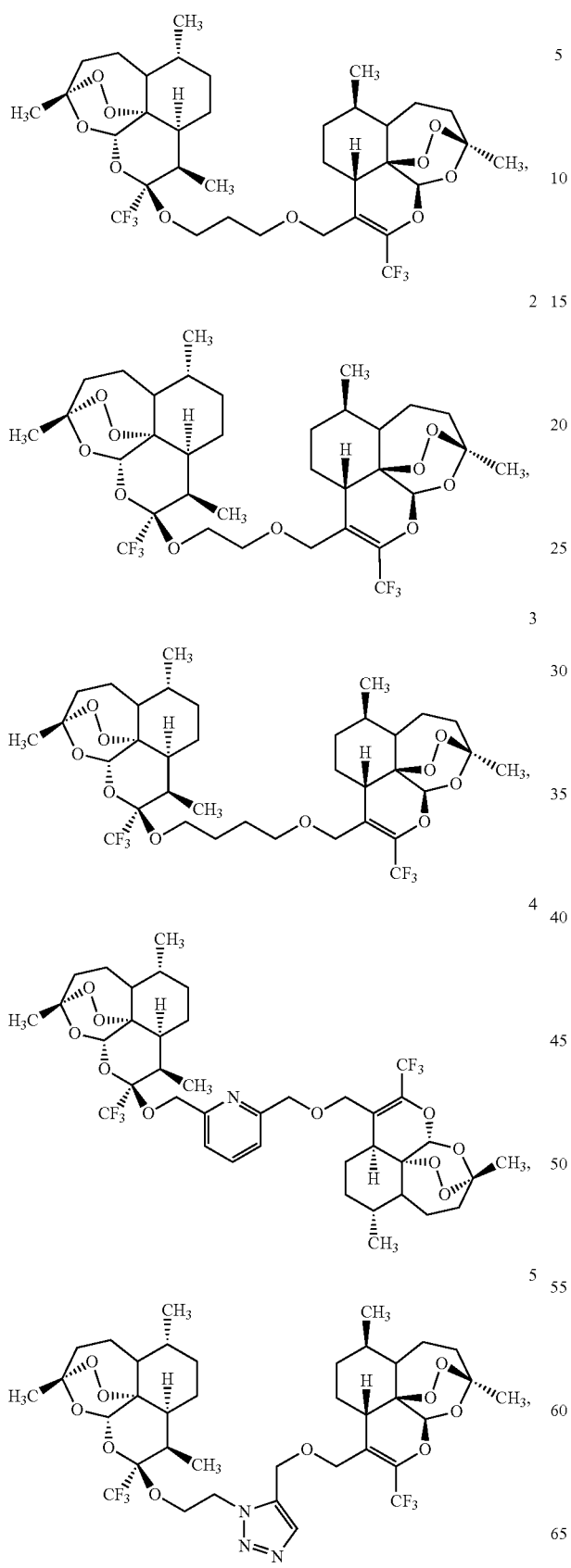

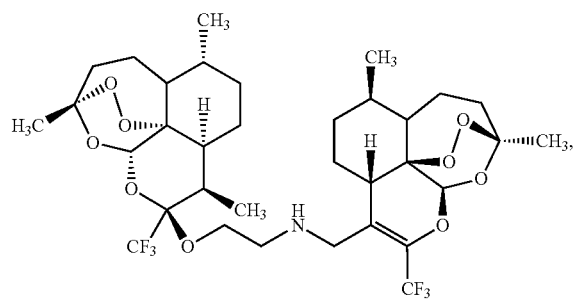
10
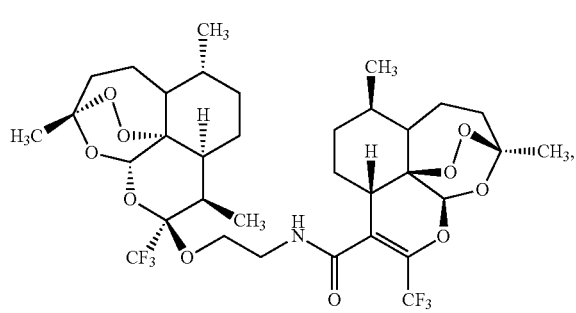
11
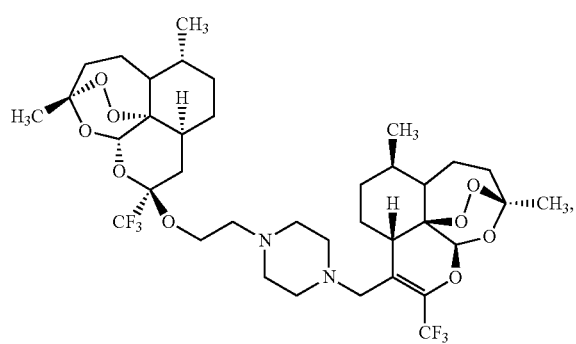
12
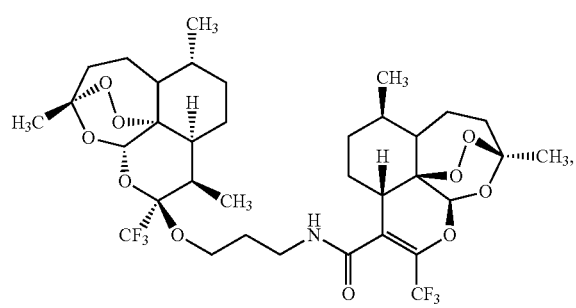
13
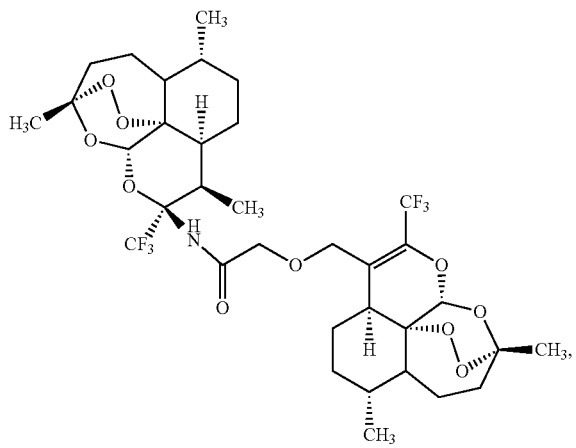
14
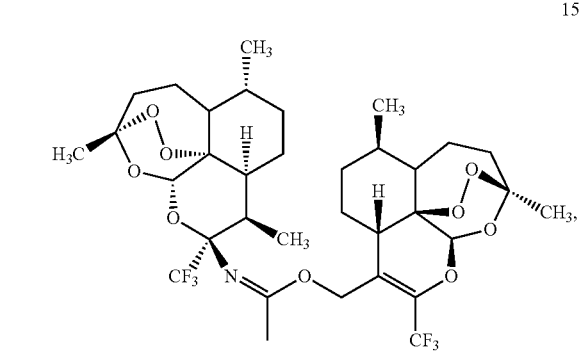
15
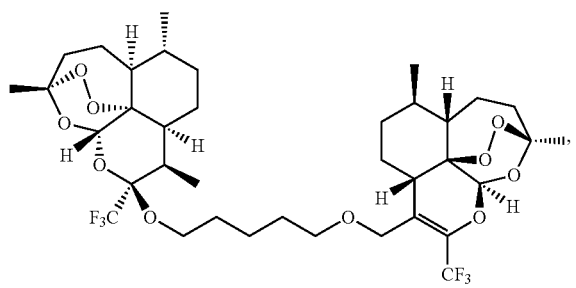
16
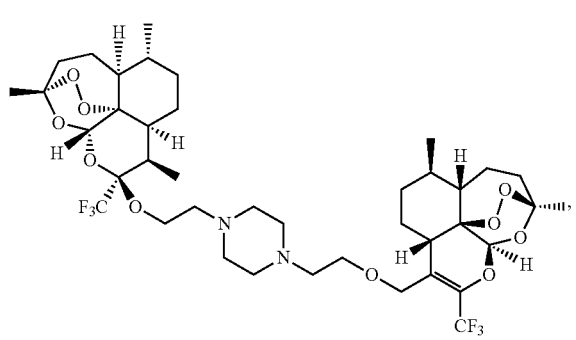
18

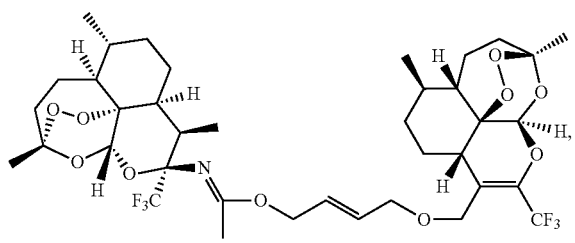

21

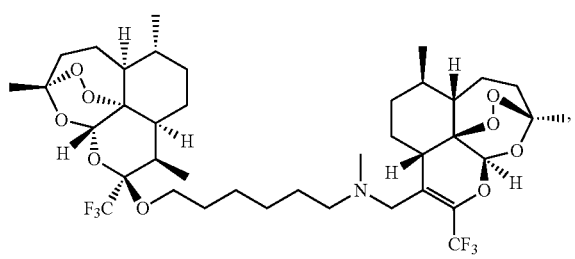

22

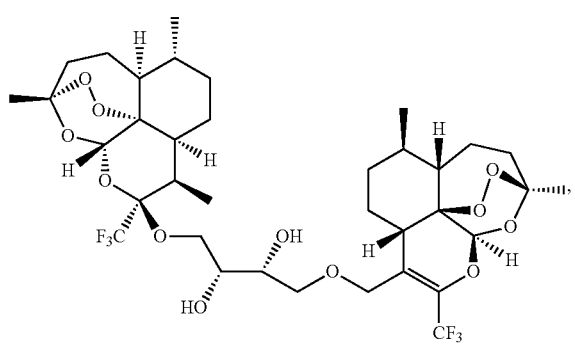

23

27

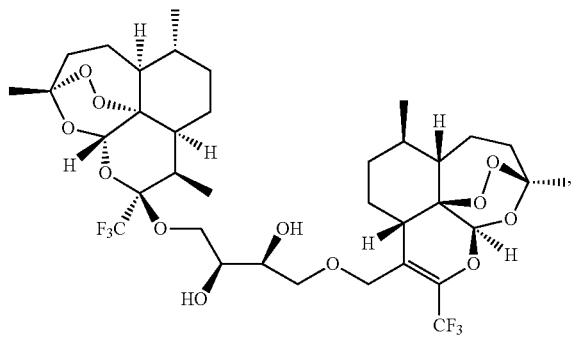

28 and

29

6. A pharmaceutical composition comprising at least one dimeric derivative according to claim 1 and at least one pharmaceutically acceptable carrier.

7. The pharmaceutical composition of claim 6 further comprising at least one other active ingredient.

8. A pharmaceutical composition comprising:

(i) at least one compound according to claim 1, and (ii) at least one other active ingredient, as combination products for a simultaneous, separated or sequential use.

9. The composition of claim 8, wherein the at least one other active ingredient is selected from anticancer agents.

10. The pharmaceutical composition according to claim 9, wherein the anticancer agent is selected from 6-mercaptopurine, fludarabine, cladribine, pentostatin, cytarabine, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocin, carboplatin, cisplatin, oxaliplatin, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrozole, letrozole, tamoxifen, octreotide and lanreotide.

* * * * *